(12) United States Patent
Yoshida et al.

(10) Patent No.: US 10,252,713 B2
(45) Date of Patent: Apr. 9, 2019

(54) VEHICULAR DRIVING CONTROL SYSTEM

(71) Applicant: DENSO CORPORATION, Kariya, Aichi-pref. (JP)

(72) Inventors: Ichiro Yoshida, Kariya (JP); Kiyohiko Sawada, Kariya (JP)

(73) Assignee: DENSO CORPORATION, Kariya, Aichi-pref. (JP)

( * ) Notice: Subject to any disclaimer, the term of this patent is extended or adjusted under 35 U.S.C. 154(b) by 222 days.

(21) Appl. No.: 15/502,559

(22) PCT Filed: Aug. 19, 2015

(86) PCT No.: PCT/JP2015/004110
§ 371 (c)(1),
(2) Date: Feb. 8, 2017

(87) PCT Pub. No.: WO2016/035268
PCT Pub. Date: Mar. 10, 2016

(65) Prior Publication Data
US 2017/0225677 A1    Aug. 10, 2017

(30) Foreign Application Priority Data

Sep. 3, 2014  (JP) ................................ 2014-179069
Jul. 14, 2015  (JP) ................................ 2015-140427

(51) Int. Cl.
*B60T 7/12*        (2006.01)
*B60W 30/02*   (2012.01)
(Continued)

(52) U.S. Cl.
CPC ......... *B60W 30/025* (2013.01); *A61B 5/0476* (2013.01); *A61B 5/18* (2013.01);
(Continued)

(58) Field of Classification Search
None
See application file for complete search history.

(56) References Cited

U.S. PATENT DOCUMENTS

2005/0240328 A1* 10/2005 Shirato .................. B62D 1/286
                                                                 701/41
2008/0119328 A1*  5/2008 Satou .................... B60W 10/02
                                                                 477/181
(Continued)

FOREIGN PATENT DOCUMENTS

JP          2009101830 A       5/2009
JP          2012022041 A       2/2012
(Continued)

*Primary Examiner* — Adam M Alharbi
(74) *Attorney, Agent, or Firm* — Harness, Dickey & Pierce, P.L.C.

(57) ABSTRACT

A vehicular driving control system for performing vehicular driving control based on automated driving and/or driving assistance is provided. The vehicular driving control system includes a driver operation measuring instrument that measures driving operation of a driver, a user uneasiness degree measuring instrument that measures how large a degree of uneasiness of a user is, and a driving control apparatus. When it is determined that the user feels uneasy based on the user uneasiness degree, the driving control apparatus determines an uneasiness factor serving as a source of the uneasiness based on user property data in relation to a traveling situation of a vehicle. Based on the determined uneasiness factor, the driving control apparatus adjusts a control degree of the vehicular driving control, and changes the vehicular driving control so as to decrease the uneasiness of the user.

7 Claims, 25 Drawing Sheets

(51) Int. Cl.
  *A61B 5/0476* (2006.01)
  *B60W 30/08* (2012.01)
  *A61B 5/00* (2006.01)
  *A61B 5/18* (2006.01)
  *B60W 30/18* (2012.01)
  *B60W 50/00* (2006.01)
  *B60W 50/10* (2012.01)
  *A61B 5/026* (2006.01)

(52) U.S. Cl.
  CPC ........... *A61B 5/6893* (2013.01); *B60W 30/08* (2013.01); *B60W 30/18* (2013.01); *A61B 5/0261* (2013.01); *A61B 5/6803* (2013.01); *B60W 50/0098* (2013.01); *B60W 50/10* (2013.01); *B60W 2050/0002* (2013.01); *B60W 2050/0071* (2013.01); *B60W 2050/0075* (2013.01); *B60W 2540/22* (2013.01); *B60W 2540/28* (2013.01); *B60W 2540/30* (2013.01); *B60W 2550/141* (2013.01); *B60W 2550/402* (2013.01)

(56) References Cited

U.S. PATENT DOCUMENTS

| | | | |
|---|---|---|---|
| 2009/0099800 A1* | 4/2009 | Ishishita | B60L 3/0046 702/63 |
| 2009/0143195 A1* | 6/2009 | Katakura | B60W 10/02 477/120 |

FOREIGN PATENT DOCUMENTS

| | | |
|---|---|---|
| JP | 2012173803 A | 9/2012 |
| JP | 2014151838 A | 8/2014 |
| WO | WO-2013080250 A1 | 6/2013 |

* cited by examiner

FIG. 13

```
Driver Property (Driving Tendency and Acceptable Range)
Name: Mr. ○○
    While driving:
        Inter-vehicular distance during normal driving
            • Traveling speed of 60 km/h
                Forward: 40 meters (20 meters shorter than average)
                Forward inter-vehicular distance of 40 meters or shorter makes the driver feel uneasy.
                Right-left: 1.0 meter
                (interval of 0.8 meters makes the ordinary feel uneasy.)
            • Traveling speed of 40 km/h
                Forward: 10 meters (10 meters shorter than average)
                Forward inter-vehicular distance of 10 meters or shorter makes the driver feel uneasy.
                Right-left: 1.0 meter
                        Interval of 0.8 m makes the ordinary feel uneasy.
        Driving style on curved roads
                Position at right curve: the center of a lane (average)
                Position at left curve: 50 cm left from the center of a lane (inner riving)
            • Traveling speed of 60 km/h
                Curvature of 50 meters makes the driver feel uneasy.
            • Traveling speed of 40 km/h
                Curvature of 40 meters makes the driver feel uneasy.
            • Lateral acceleration (curved road driving) 0.5G makes driver feel uneasy.

Braking
            • Normal braking (backward and forward) -0.3 g
                (smaller absolute value than average of 0.4 g)
Others
Wobble (traveling position)
Vibration
Sound
```

FIG. 14

Passenger Property  
Name: Mr. ○○  
Onboard (passenger seat) (rear seat  
  Response to inter-vehicular distance during normal driving  
    • Traveling speed of 60 km/h  
     Forward: 60 meters (average)  
     Right-left: 1.5 meters  
    • Traveling speed of 40 km/h  
     Forward: 40 meters (average)  
     Right-left: 1 m  
       Interval of 0.8 m makes the passenger feel uneasy.  
  Driving style on curved roads  
    Position at right curve: the center of a lane (average)  
    Position at left curve: the center of a lane (average)  
    • Traveling speed of 60 km/h  
     Curvature of 200 meters makes the passenger feel uneasy.  
    • Traveling speed of 40 km/h  
     Curvature of 100 meters makes the passenger feel uneasy.  
    • Lateral acceleration (curved road driving) 0.4 G makes passenger feel uneasy.  
  Braking  
    • Normal braking (backward and forward) -0.3 g  
     (smaller absolute value than average of 0.4 g)

Others  
Wobble (traveling position)  
Vibration  
Sound

VEHICULAR DRIVING CONTROL SYSTEM

CROSS REFERENCE TO RELATED APPLICATIONS

This application is a U.S. National Phase Application under 35 U.S.C. 371 of International Application No. PCT/JP2015/004110 filed on Aug. 19, 2015 and published in Japanese as WO 2016/035268 A1 on Mar. 10, 2016. This application is based on and claims the benefit of priority from Japanese Patent Applications No. 2014-179069 filed on Sep. 3, 2014 and No. 2015-140427 filed on Jul. 14, 2015.The entire disclosures of all of the above applications are incorporated herein by reference.

TECHNICAL FIELD

The present disclosure relates to a vehicular driving control system configured to provide vehicular driving control with automated driving (including driving assistance).

BACKGROUND ART

Recently, a vehicle is mounted with an automated driving apparatus or a driving assistance apparatus to perform driving control based on automated driving (including driving assistance). A driving style of the automated driving may differ from a user's ordinary manual operation-based driving style if the user (driver or fellow passenger) is not accustomed to the driving style of the automated driving. The driving style of the manual operation differs from user to user and reflects the driver's habit (individuality) because the manual operation is related to a user's (driver's) stance on the safety. The driver may feel uneasy when the driving style of the automated driving greatly differs from the user's ordinary manual operation-based driving style even though the vehicle appropriately performs the driving control with the automated driving. A fellow passenger may be accustomed to the driver's ordinary driving style. The fellow passenger may also feel uneasy when the driving style of the automated driving greatly differs from the user's ordinary manual operation-based driving style.

PRIOR ART LITERATURES

Patent Literature

Patent Literature 1: JP-2012-22041A

SUMMARY OF INVENTION

An apparatus described in patent literature 1 estimates feeling of a driver when receiving driving assistance and improves a driving technique of the driver by controlling the amount of driving assistance so that driver is assumed to be able to feel pleasant. However, the inventors of the present disclosure found that the configuration according to patent literature 1 may also cause a difference between a driving style resulting from the driving assistance and the driver's ordinary driving style. In this case, the driver or a fellow passenger feels uneasy.

It is an object of the invention to provide a vehicular driving control system capable of well preventing a user from feeling uneasy despite provision of driving control with automated driving and/or driving assistance.

In an example of the present disclosure, a vehicular driving control system for performing vehicular driving control with automated driving and/or driving assistance is provided. The vehicular driving control system comprises: a driver operation measuring instrument that measures driving operation of a driver; a user uneasiness degree measuring instrument that measures how large a degree of uneasiness of a user is; and a driving control apparatus. On condition of the user determined to feel uneasy based on a result of measuring the user uneasiness degree measured by the user uneasiness degree measuring instrument, the driving control apparatus determines an uneasiness factor serving as a source of the uneasiness based on user property data in relation to a traveling situation of a vehicle. Based on the determined uneasiness factor, the driving control apparatus adjusts a control degree of the vehicular driving control, and changes the vehicular driving control so as to decrease the uneasiness of the user.

The vehicular driving control system can well prevent a user from feeling uneasy despite provision of driving control with automated driving or driving assistance.

BRIEF DESCRIPTION OF DRAWINGS

The foregoing and other objects, features and advantages of the disclosure will become more apparent from the detailed description given below with reference to the accompanying drawings in which:

FIG. 13 is a diagram illustrating an example of driver property data (emotion data);

FIG. 14 is a diagram illustrating an example of fellow passenger property data (emotion data);

EMBODIMENTS FOR CARRYING OUT INVENTION

Figure 1:
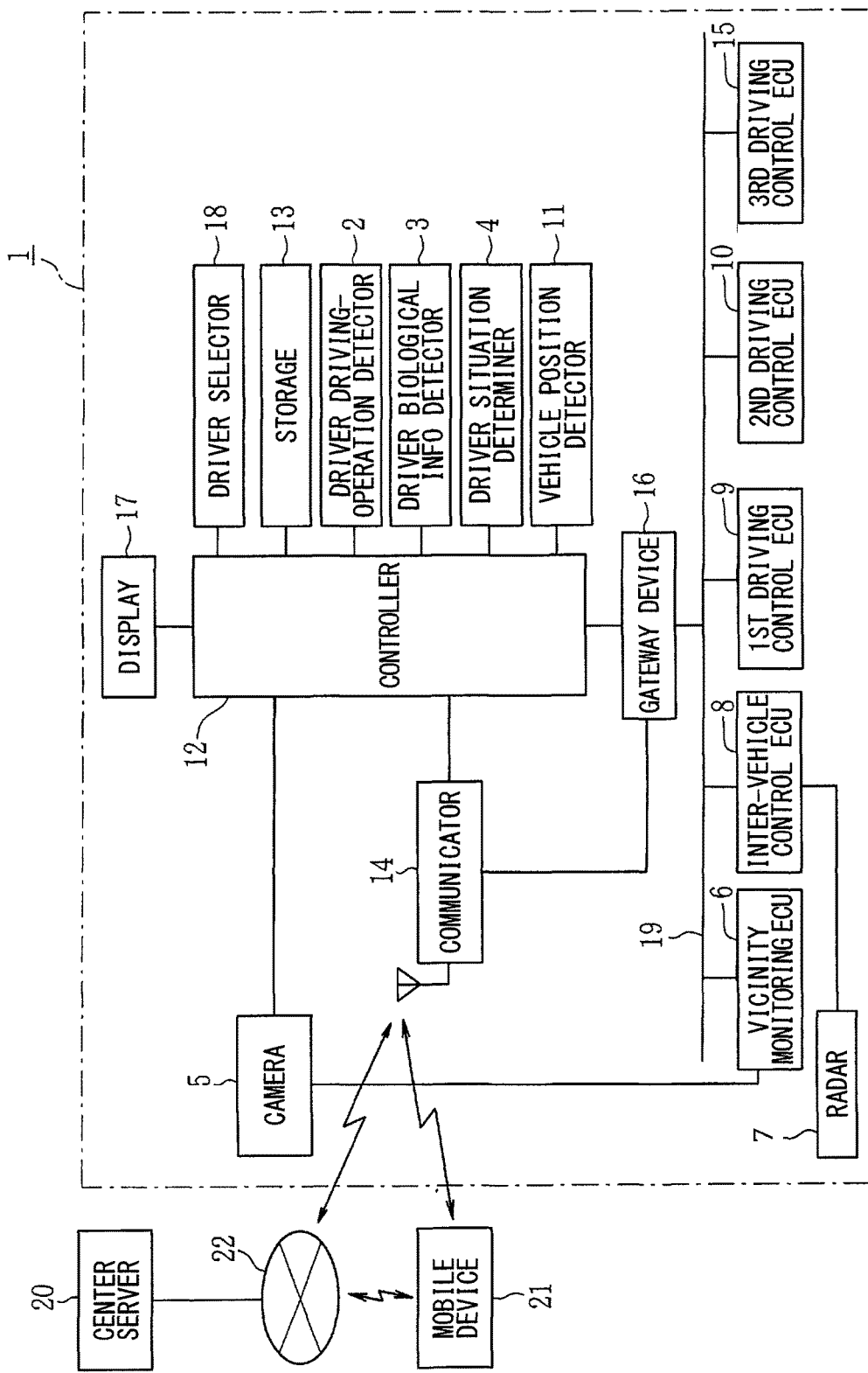
FIG. 1 is a block diagram illustrating a vehicular driving control system according to a first embodiment.

A first embodiment will be described with reference to FIGS. 1 through 27B. FIG. 1 is a block diagram illustrating a vehicular driving control system according to the embodiment. As illustrated in FIG. 1, a vehicular driving control system 1 includes a driver driving-operation detector 2, a driver biological information detector 3, a driver situation determiner 4, a camera 5, a vicinity monitoring ECU (electronic control unit) 6, a radar 7, an inter-vehicle control ECU 8, a first driving control ECU 9, a second driving control ECU 10, a third driving control ECU 15, a subject vehicle position detector 11, a controller 12, a storage 13, a communicator 14, a gateway device 16, a display apparatus 17, and a driver selector 18.

The driver driving-operation detector 2 detects driving operation of a driver and outputs a detection signal. Specifically, the driver driving-operation detector 2 detects a speed or accuracy of the driver's driving operation (to manipulate an accelerator, a brake, or a steering system) based on a sensor signal from an angle sensor (unshown) attached to the accelerator, the brake, or the steering system. The driver driving-operation detector 2 corresponds to an example of a driver operation measuring instrument.

The driver biological information detector 3 detects the driver's biological information and outputs a detection signal. Specifically, the driver biological information detector 3 detects conscious or emotional situations of a user (driver or fellow passenger) by using various sensors (unshown) to measure an electrocardiogram, a heart rate, a blood pressure, or sweating or a brain activation region measuring instrument 23 (see FIGS. 11A and 11B) to measure distribution of brain activation regions. In this case, the various sensors and the brain activation region measuring instrument 23 for the driver biological information detector 3 are advantageously configured as wearable sensors that can be attached to clothes or a hair accessory in order to acquire biological information about a driver or a fellow passenger.

Detection information detected by the driver driving-operation detector 2 and the driver biological information detector 3 is input to the driver situation determiner 4 that determines a driver (user) situation. Based on the input information, the driver situation determiner 4 determines physical status of the driver while traveling or mental status of the driver or a fellow passenger. The driver situation determiner 4 outputs information about the determination to the controller 12. The physical status while traveling includes states of a muscular response of limbs or a visual sense (visual field or dynamic visual acuity). The mental status includes an emotional (psychological) state estimated based on measurement information such as a heart rate, a blood pressure, or brain waves. The driver situation determiner 4 corresponds to an example of a user uneasiness degree measuring instrument.

The camera 5 includes a plurality of cameras that capture a situation outside the vehicle. The captured image information is output to the vicinity monitoring ECU 6 and the controller 12. The vicinity monitoring ECU 6 recognizes the situation around the vehicle (correspondence between a position and an object) based on the image information captured by the camera 5 and outputs the recognized perimeter monitoring information to the controller 12 via an onboard LAN 19. The vicinity monitoring ECU 6 corresponds to an example of a widthwise traveling position detection apparatus.

The radar 7 includes a function to detect a distance and a direction toward an object (around the vehicle) such as a vehicle or a pedestrian around the vehicle by using a microwave or a laser. The radar 7 outputs detected object detection information to the inter-vehicle control ECU 8. The inter-vehicle control ECU 8 is supplied with the object detection information around the vehicle and, based on the object detection information, controls traveling (braking and acceleration) of the vehicle so as not to collide with an object around the vehicle. The radar 7 corresponds to an example of an inter-vehicular distance detection apparatus.

The first driving control ECU 9 is supplied with the object detection information around the vehicle via the onboard LAN 19 and, based on the object detection information around the vehicle, controls traveling (braking and acceleration) of the vehicle in a front-back direction. The second driving control ECU 10 is supplied with the object detection information around the vehicle via the onboard LAN 19 and, based on the object detection information around the vehicle, controls traveling (manipulation such as steering, braking, and acceleration) of the vehicle in a horizontal direction. The third driving control ECU 15 is supplied with the object detection information around the vehicle via the onboard LAN 19 and, based on the object detection information around the vehicle, controls traveling (speed, control over variable damper attenuation, braking, and acceleration) of the vehicle in a vertical direction.

The subject vehicle position detector 11 measures a position of the subject vehicle as latitude and longitude information by using GPS (unshown). The subject vehicle position detector 11 outputs vehicle position measurement information to the controller 12. The controller 12 controls automatic traveling of the vehicle based on the vehicle position measurement information or the object detection information around the vehicle. The controller 12 configures a device for master control. The controller 12 corresponds to an example of a driving control apparatus.

Each ECU information or measurement information may be exchanged among the ECUs (the inter-vehicle control ECU 8, the first driving control ECU 9, the second driving control ECU 10, the third driving control ECU 15, and the controller 12) via the onboard LAN 19. Autonomous operations of the ECUs may collaborate to control automatic traveling of the vehicle (referred to as collaborative control). To perform the collaborative control, the onboard LAN 19 is advantageously configured as a fast onboard network so that information can be fast exchanged between the ECUs for driving control. Advantageously, the fast onboard network provides a high communication speed and uses an optical fiber capable of multi-channel communication that can simultaneously transmit a plurality of pieces of ECU data to other ECUs. In this case, the communication may be configured so that a data header includes data that indicates a degree of urgency of the information output from each ECU. This can provide safe vehicular driving control.

According to the embodiment, the controller 12 may determine that the road environment prevents recognition of a road situation because the camera 5 or the radar 7 hardly measures the road situation in which the vehicle travels. For example, a road shape greatly varies and trees hide the road shape ahead or a building causes poor visibility ahead. In such a case, the controller 12 performs preliminary determination based on the camera image information and "road shape data" recorded in the storage 13.

The preliminary determination estimates what exists at a position invisible from the camera (driver) 5, based on information such as a map database or a road shape database recorded in the storage 13. The preliminary determination determines what control (deceleration or steering manipulation) is needed for safe traveling. The preliminary determination provides necessary information for each ECU. This is referred to as a protective automated driving that provides the preparation allowing the automated driving to contribute to ensure safety of the driver.

According to the embodiment, the driver biological information detector 3, the driver driving-operation detector 2, and the subject vehicle position detector 11 measure what reaction the driver shows at which place or in which traveling condition (automated driving or manual operation). Measurements are used for the driving control in real time and are recorded in the storage 13 so that the data is analyzed later to be used for estimation control. In this case, the data is recorded as driver property data. The communicator 14 transmits information about actions or reactions characteristic of the driver to a center server 20 via a wireless communication network (e.g., mobile telephone communication network) 22. The information is recorded in the center server 20 as needed.

The controller 12 can communicate with a mobile device 21 such as a smartphone (external device) via the communicator 14. The mobile device 21 can remotely control the vehicle. In this case, a remote control application is advantageously installed on the mobile device 21 in order to remotely control the vehicle. From the viewpoint of security, there may be provided an additional remote controller (unshown) that enables remote control operation only in response to input of specific information (e.g. biological information or a brain wave pattern of the user).

If the mobile device 21 is available near the vehicle, the communicator 14 can use a communication device compliant with the communication system such as NFC (Near Field Communication) or DSRC (Dedicated Short Range Communication), for example. If the mobile device 21 is placed far from the vehicle, the communicator 14 can use a mobile device compliant with the communication that uses the wireless communication network (e.g., mobile telephone communication network) 22.

The center server 20 of an information center transmits information necessary for the vehicle. The controller 12 can receive this information via the communicator 14. Advantageously in this case, the communicator 14 is provided as a device compliant with wireless communication using a mobile telephone communication network or a wireless device referred to as a WiFi communication instrument compliant with communication using the Internet via wireless LAN. Communication data processed by the communicator 14 of the vehicle is transmitted to the gateway device 16 mounted on the vehicle. The gateway device 16 checks received data. If the received data is normal, the gateway device 16 transmits the received data to various ECUs via the onboard LAN 19. The gateway device 16 includes a "remote control data determination function (authentication function)." This function determines whether remote control data is correct and produces a valid control result (causing no accident or no harm to a user) when the gateway device 16 receives the remote control data that is transmitted from the external mobile device 21 and includes a request to change a traveling situation of the vehicle.

When the gateway device 16 transmits information to the controller 12, the controller 12 determines the transmitted information and performs a necessary process. When surrounding traffic information data is transmitted from outside the vehicle, for example, the controller 12 advantageously allows the display apparatus 17 to display traffic information (e.g., a degree of congestion) overlapped with a map based on the traffic information data.

The storage 13 stores road shape data. The road shape data stores an automated driving exclusive road, an automated driving preference road (mixing of manual operation and automated driving), a manual operation exclusive road, and a road where automated driving is available to only a vehicle whose automated driving accuracy (performance) is higher than or equal to a predetermined setting. Namely, the road shape data stores automated driving categories as road characteristics. The display apparatus 17 displays a map, if available, and the automated driving category of a nearby road on the map.

The controller 12 may determine that the automated driving needs to be changed to the manual operation while the vehicle travels a specified road by using an automated driving function of the driving control system 1. In this case, the driver is notified of the necessity to change to the manual operation by using a notifier (display apparatus 17), an audio output apparatus (unshown), or seat vibration of the vehicle. The driver may not respond to the notification to the driver.

In such a case, stimulation to activate the consciousness (brain) may be supplied to alert the driver. A steering system or a wearable device can generate sound, vibration, or weak electric current for the stimulation. The driver situation determiner 4 may determine whether the notification causes an effect on the driver. The notification may continue until the driver is certainly alerted.

The embodiment provides a driver selector 18 to determine (select) a driver based on an electronic key or a mobile device carried by the driver or recognition using a camera image of the driver in consideration of a case where the driver is changed. The safety (security) further improves when a driver is verified by using a database to determine the driver (user) registered to the center server 20 while the driver selector 18 determines the driver.

The vehicular driving control system 1 according to the embodiment performs an automated driving for driving control and may cause driving that makes the driver (or a fellow passenger) feel uneasy. To solve this, the driving control system 1 according to the embodiment daily acquires correlative relationship between a driving condition and uneasiness of the driver or the fellow passenger. The storage 13 stores a vehicular traveling situation (e.g., driving condition) that easily causes uneasiness. For example, the storage 13 stores a traveling situation that causes a substantial correlative relationship between a traveling position of the vehicle and a place where uneasiness occurs.

Advantageously, a change of operation mode (automated driving or manual operation) is accompanied by notification corresponding to a user property (personality or athletic ability) in order to ensure the safety of the user (driver or fellow passenger). A user may increase uneasiness due to a sudden notification. Advantageously, the driving control system 1 records a notification procedure on a user basis and modifies or configures the notification procedure so that the user can accept notification timing, a magnitude of notification sound, or display visibility without uneasiness.

The description below explains an example of data concerning driving conditions (vehicle manipulation) detected and collected by the driver driving-operation detector 2. The data affects vehicle traveling. Depending on a data value, the user can feel that the vehicle travels safely or unsteadily.

Data concerning the start of driving (start or stop manipulation, the time from the start of energization to operation, or the time to start traveling)

Uneasiness about the vehicle especially increases if the automated driving causes an unstable driving control operation at the beginning.

Data concerning a gear change (to go forward or backward)

During manual operation, the user increases uneasiness if the gear change is unsmooth. During automated driving, the user increases uneasiness if the operation is unnatural (causing unnecessary vibration or sound).

The user feels uneasy without vehicle traveling preferred by the user, namely, driving operations ordinarily performed by the user as regards five items of data below.

Data concerning acceleration (accelerator response)
Data concerning deceleration (brake response)
Data concerning cornering (steering response)
Data concerning vehicle width control (horizontal control or vehicle width interval)
Data concerning inter-vehicular control (front-back control or distance interval)

The following four items of data are needed for the user to determine safety while driving.

Data concerning driving stabilization control (stabilizer)
The user feels uneasy if the vehicle vibration remains.
Data concerning a vehicle height change
Wide visibility or ease of confirming situations near the vehicle makes the user feel easier.
Data concerning onboard lighting system activation or direction control (illuminance sensor)
Degrading the visibility at night makes the user feel uneasier.
Data concerning ambient images
Degrading the visibility of a dead zone makes the user feel uneasier.

The following functions affect driving of the driver.
Audio volume
The user may feel uneasy depending on a sound volume or a volume of sound of a high or low frequency.
Seat position
Improved visibility is desirable during driving or a backrest angle needs to be changed to relax during rest time.
Wiper operation
The wiper operation needs to be automatically improved because the manual operation is unreliable due to poor visibility in case of rain.
Door lock operation
The user may be unsure about whether the door is locked unfailingly.
This may make the user uneasy.
Door window operation
The user may be irritated if opening or closing a window glass cannot be adjusted to a user-specified position.

The embodiment detects how the user biologically reacts to a vehicle operation. To do this, the user's heart rate, blood pressure, or sweating is measured by a sensor attached to the steering system or the brain activation region measuring instrument 23 (see FIGS. 11A and 11B) attached to adhere tightly to the human head skin. Brain waves are measured by a sensor placed near the head surface or a sensor attached to adhere tightly to the head. The brain is considered to include a part to process instinctive reactions and another part to process rational reactions. The different parts react to pleasure and uneasiness. The brain activation region measuring instrument 23 can be used to measure what emotion the user feels. Only measurement of an activated brain region can determine the user emotion by acquiring correlative relationship between the user emotion resulting from the user's conversation or voice and an activated region in the brain and recording the result. A specific configuration of the brain activation region measuring instrument 23 according to the embodiment will be described later.

The description below explains collection and recording of occupant information according to the embodiment. The driver driving-operation detector 2, the driver biological information detector 3, and the subject vehicle position detector 11 measure vehicle operations and user reactions. Measurement result information is recorded as the occupant information. An advantageous recording method is to record the occupant information during a predetermined time interval from the past to the present by using a drive recorder that captures and records scenery outside the vehicle by using a camera. For example, the storage 13 of the driving control system 1 always records the updated occupant information in past ten minutes from the present. When a recording condition is satisfied, older occupant information is advantageously recorded in the storage 13, the memory in the mobile device 21, or a storage (storage medium) of the center server 20 outside the vehicle.

A biological sensing item of the user may increase the sensing quantity. In such a case, the storage 13 stores information 1, namely, related sensing information and vehicle information (the control quantity of the ECUs included in the driving control system 1) from a time point to increase the sensing quantity to a time point in the past. A sensing item may increase the sensing quantity and then return to a normal state (value). In such a case, the storage 13 stores information 2, namely, related sensing information and vehicle information from a time point to increase the sensing quantity to a time point to return to the normal state.

Information 1 and information 2 can be used to analyze what made the user to increase the sensing quantity of the sensing item and how the sensing quantity returns to a stable level (original state). Storing and analyzing this type of data can recognize what motion (traveling) of the vehicle causes the user to give what reaction. The user emotion can be determined from activation patterns of brain waves, making it possible to measure the presence or absence of uneasiness or the degree of uneasiness.

The description below explains an example of supporting the user based on the collected information. Correspondence between reaction data from biological sensors and map information or road information can help recognize what consciousness or emotion the user feels depending on what place or driving operation. For example, suppose that the user reacts similarly when the vehicle passes through the same place several times. The data can be evaluated to be highly reliable. When the highly reliable data is acquired, a predicted operation can be prepared or the notifier can provide driving assistance so that safer operation (driving control) can be performed in response to the user reaction at that place.

For example, suppose that the user often overlooks a pedestrian on the road at a given place while driving the vehicle. In such a case, the traveling speed is decreased to prevent the user from overlooking an object (pedestrian). Alternatively, an ambient monitoring level is increased to notify the user of the situation around the vehicle as early as possible.

The embodiment provides control to change between operation modes based on the occupant information, namely, from an automated driving mode to a manual operation mode or from the manual operation mode to the automated driving mode. For example, a user state is detected at the time to change the operation mode. The operation mode is changed when the operation mode can be changed safely without uneasiness of the user.

Figure 2:
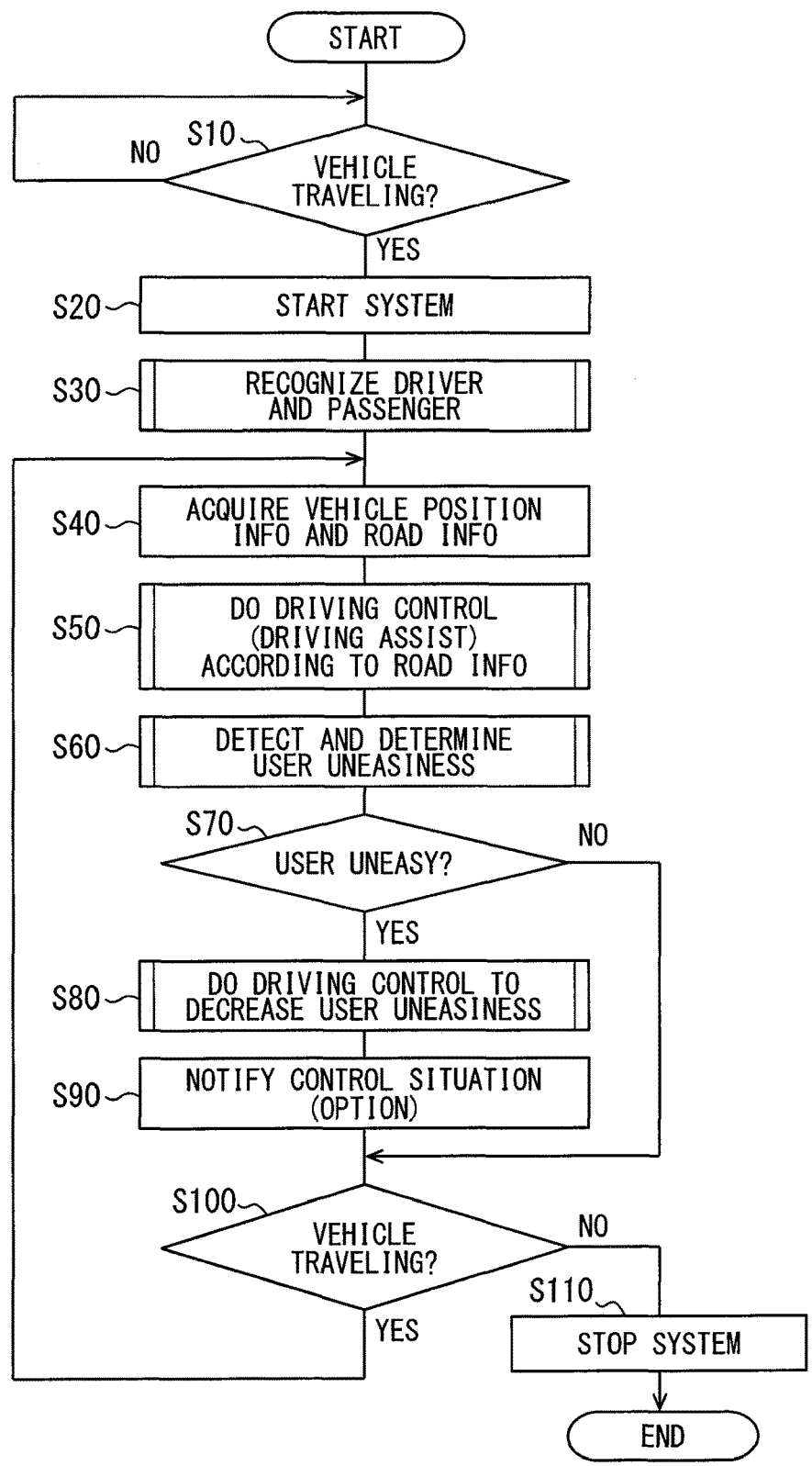
FIG. 2 is a flowchart illustrating a main control of the vehicular driving control system.

FIGS. 2 through 8 are flowcharts illustrating the contents of control performed by the vehicular driving control system 1 (controller 12) according to the embodiment. The flowchart in FIG. 2 illustrates the contents of a main control that detects uneasiness of the user and performs driving control to reduce the uneasiness. The main control is described below.

At S10 in FIG. 2, the controller 12 determines whether the vehicle is traveling. If the vehicle is determined to be traveling, the controller 12 proceeds to "YES" and starts the system (S20). The controller 12 proceeds to S30 to perform a recognition process on the user (driver or fellow passenger). The recognition process will be described specifically with reference to a subroutine flowchart in FIG. 3.

The controller 12 subsequently proceeds to a periodic operation. The controller 12 proceeds to S40. The driving control system 1 acquires position information about the vehicle and information about a road traveled by the vehicle. The controller 12 proceeds to S50 and performs driving control or driving assistance corresponding to the road information. The driving control or driving assistance process will be described later with reference to a subroutine flowchart in FIG. 6.

The controller 12 proceeds to S60 and detects and determines uneasiness of the user while performing the vehicular driving control. The uneasiness detection and determination process will be described later with reference to a subroutine flowchart in FIG. 5.

The controller 12 proceeds to S70 and determines whether the user feels uneasy. If the user is determined to feel uneasy, the controller 12 proceeds to "YES" and proceeds to S80 to perform the vehicular driving control to decrease uneasiness of the user. The driving control process will be described later with reference to a subroutine flowchart in FIG. 8. The controller 12 proceeds to S90 and notifies a control situation if the control situation needs to be notified due to a control change.

The controller 12 proceeds to S100 and determines whether the vehicle is traveling. If the vehicle is traveling, the controller 12 proceeds to "YES" and returns to S40 to repeat the above-mentioned process. If the vehicle is not traveling at S100, the controller 12 proceeds to "NO" and proceeds to S110 to stop the driving control system 1.

If the user does not feel uneasy at S70, the controller 12 proceeds to "NO" and proceeds to S100 to repeat the above-mentioned process. The driving control system 1 may be placed in a quiescent state at S110 when the vehicle temporarily stops, not completely stops (for a long time).

The description below explains the user (driver or fellow passenger) recognition process subroutine with reference to the flowchart in FIG. 3.

Figure 3:
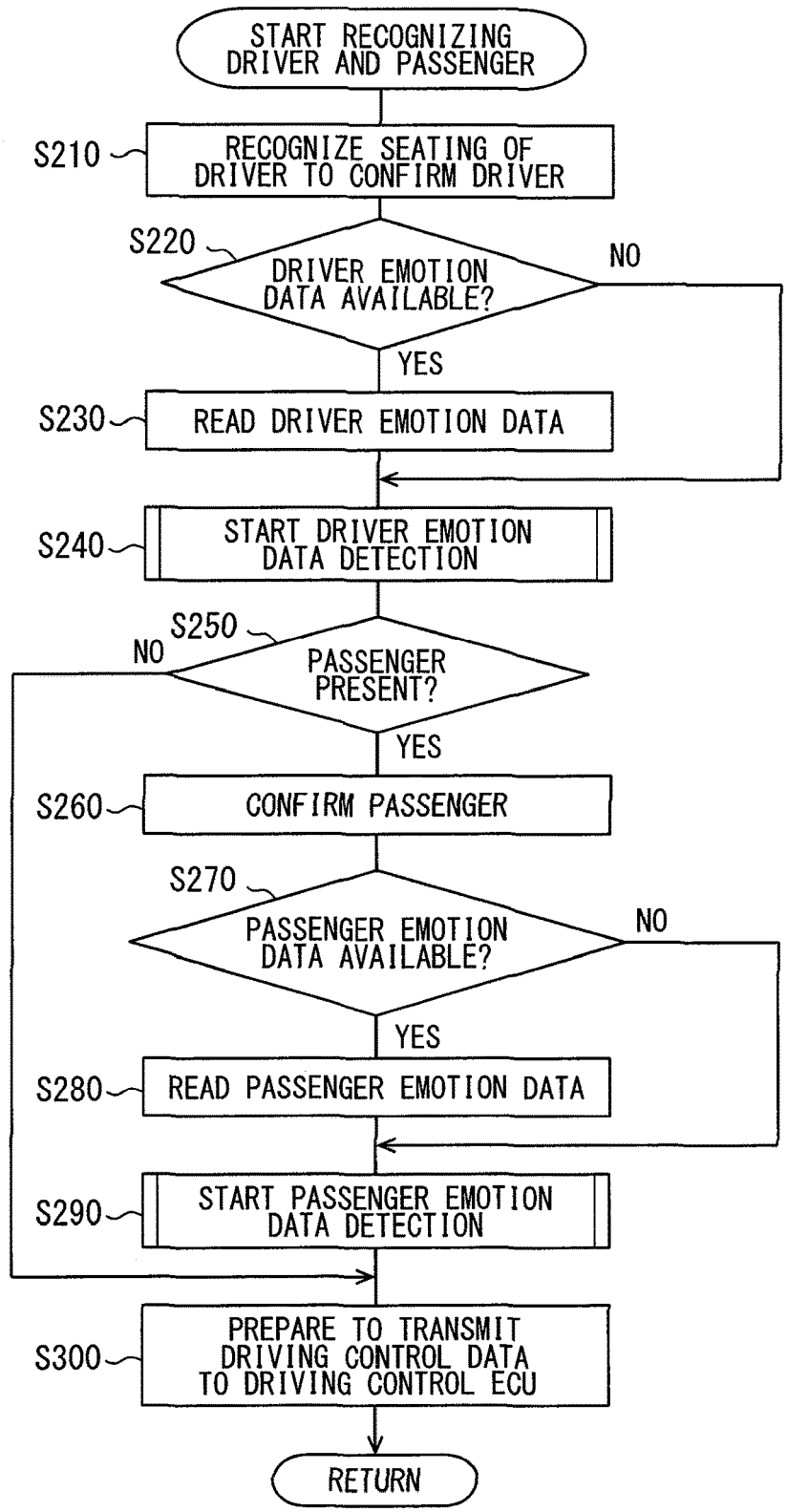
FIG. 3 is a flowchart illustrating a user (driver or fellow passenger) recognition process.

At S210 in FIG. 3, the controller 12 recognizes seating of the driver and confirms who the driver is. After confirming the driver, the controller 12 proceeds to S220 and determines whether emotion data about the driver is stored. The emotion data records what uneasiness the driver feels on what road and in which traveling state. In this case, the controller 12 searches the storage 13 of the driving control system 1, the center server 20 at a remote place, or the mobile device 21 carried by the user to confirm whether the emotion data about the driver is available. If the vehicle is driven by the user for the first time, the controller 12 confirms availability of the emotion data by accessing the center server 20 that records the user information.

If the emotion data about the driver is found at S220, the controller 12 proceeds to "YES" and proceeds to S230. The emotion data is read and is stored in the storage 13 of the driving control system 1. The emotion data is used to previously predict what uneasiness the driver feels depending on situations of a route to be traveled. If no emotion data about the user is found at S220, the controller 12 proceeds to "NO" and proceeds to S240.

The controller 12 proceeds to S240 and starts a process to detect the emotion data (uneasiness degree) about the driver. The uneasiness degree detection process will be described later with reference to a subroutine flowchart in FIG. 4.

The controller 12 proceeds to S250 to determine whether a fellow passenger is present. If the fellow passenger is present, the controller 12 proceeds to "YES" and proceeds to S260 to confirm who is the fellow passenger, similarly to the process to confirm the driver (S210) as above. The controller 12 proceeds to S270 to determine whether emotion data about the fellow passenger is available. If the emotion data about the fellow passenger is available, the controller 12 proceeds to "YES" and proceeds to S280 to read the emotion data about the fellow passenger and store it in the storage 13 of the driving control system 1.

The controller 12 proceeds to S290 to start the process to detect emotion data (uneasiness degree) about the fellow passenger. The uneasiness degree detection process will be described later with reference to a subroutine flowchart in FIG. 4.

The controller 12 proceeds to S300 and prepares to transmit a driving condition (driving control data) to the ECUs for driving control based on a measurement value in the emotion data about the driver or the fellow passenger. The driving condition is assumed to be likely to make the driver or the fellow passenger feel uneasy.

If no fellow passenger is present at S250, the controller 12 proceeds to "NO" and proceeds to S300 to perform the above-mentioned process. The process to detect the emotion data about the driver at S240 and the process from S250 to S290 are performed in parallel.

With reference to a flowchart in FIG. 4, the description below explains a subroutine to detect emotion data (uneasiness degree) about the user (driver or fellow passenger). The detection process in FIG. 4 measures the user's uneasiness degree (heartbeat, blood pressure, or brain waves) and concentration on driving.

Figure 4:
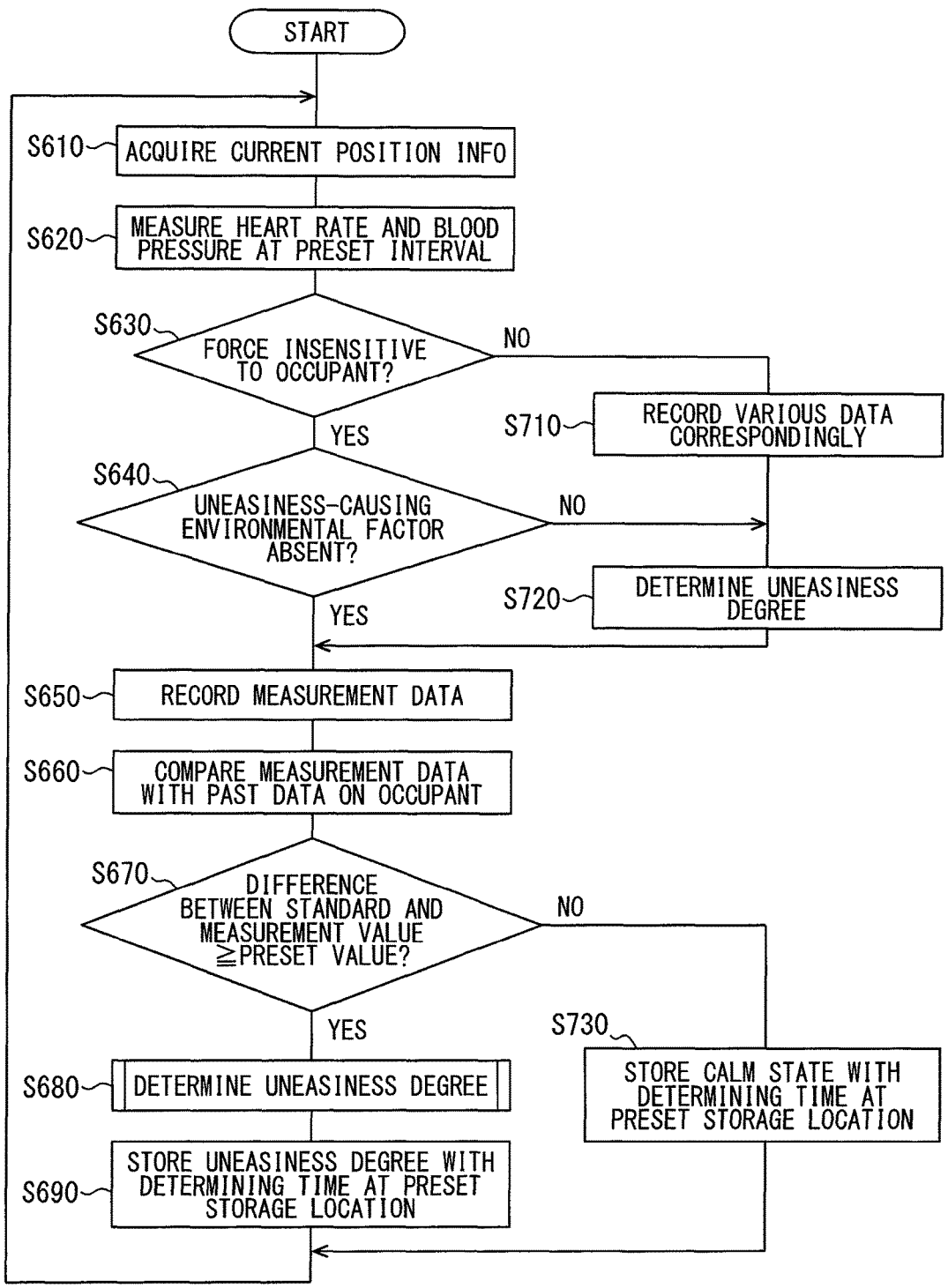
FIG. 4 is a flowchart illustrating an uneasiness degree detection process.

At S610 in FIG. 4, the controller 12 acquires current position information about the vehicle. The current position information helps to later retrieve where the user (driver or fellow passenger) went into what state. The controller 12 proceeds to S620 and measures the user's heart rate and blood pressure at a time interval of 10 seconds from the beginning of the measurement, for example.

The controller 12 proceeds to S630 and determines whether a force (acceleration, deceleration, or horizontal force) is applied to the user (occupant), namely, whether an acceleration (force) is larger than a predetermined value, while the vehicle is traveling. If no force is applied, the controller 12 proceeds to "YES" and proceeds to S640 to determine whether there is a surrounding environmental factor (object or road) that makes the user uneasy. If there is no environmental factor that makes the user uneasy, the controller 12 proceeds to "YES" and proceeds to S650 to record the measurement data in the storage 13.

If a force (acceleration) felt by the user is detected at S630, the controller 12 proceeds to "NO" and proceeds to S710. At S710, the controller 12 simultaneously or correspondingly stores time to detect the acceleration (recording of the time to start detecting the acceleration), acceleration magnitude, acceleration type, position information (road information), and user's heart rate and blood pressure in the storage 13. The controller 12 proceeds to S720 to record the measurement start time and the information about the surrounding environment in the storage 13. The controller 12 measures a position (brain wave map) where brain waves occur. Based on a change in brain wave patterns, the controller 12 estimates or determines an uneasiness degree, namely, the presence or absence of occupant's uneasiness, a type or magnitude of the uneasiness. If there is an environmental factor to cause uneasiness at S640, the controller 12 also proceeds to "NO" and proceeds to S720 to perform the above-mentioned process. The controller 12 proceeds to S650 to record the measurement data in the storage 13.

The controller 12 proceeds to S660 to compare the measurement data with user's past data (stored normal-state data). The controller 12 proceeds to S670 to determine whether a difference between the standard state (normal-state data) and the measurement value (measurement data) is larger than or equal to a predetermined value. If a difference between the standard state and the measurement value is larger than or equal to the predetermined value, the controller 12 proceeds to "YES" and proceeds to S680 to determine an uneasiness degree based on the difference between the values. The uneasiness degree determination process will be described later with reference to a subroutine flowchart in FIG. 5.

The controller 12 proceeds to S690 to store the determination result of the uneasiness degree along with the determination time at a predetermined storage location in the storage 13. The controller 12 then returns to S610 and repeats the above-mentioned process. If a difference between the standard state and the measurement value is not larger than or equal to the predetermined value, the controller 12 proceeds to "NO" and proceeds to S730 to store a calm state along with the determination time at a predetermined storage location in the storage 13. The controller 12 then returns to S610 and repeats the above-mentioned process.

Figure 9:
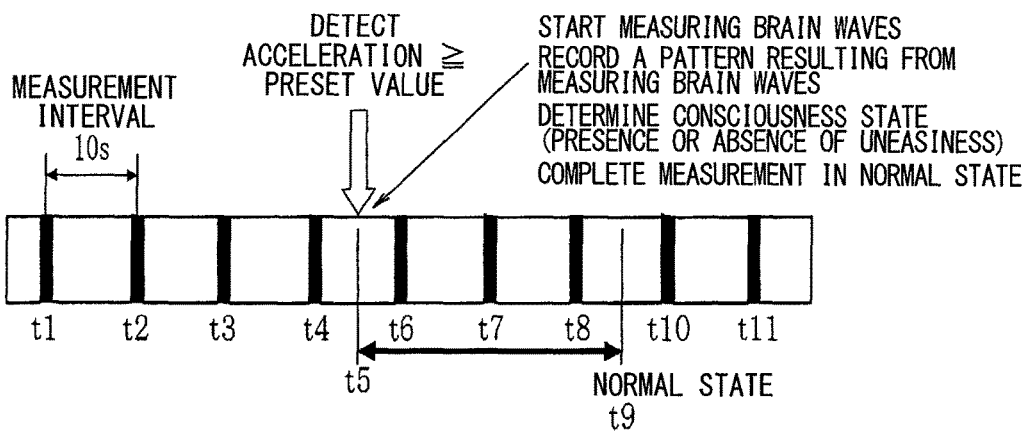
FIG. 9 is a time chart illustrating an uneasiness degree detection process.

FIG. 9 is a time chart illustrating the process to detect an uneasiness degree. As illustrated in FIG. 9, the controller 12 measures a heart rate and a blood pressure at a 10-second interval (times t1, t2, t3, and t4) regardless of the presence or absence of acceleration. Suppose that the controller 12 detects an acceleration larger than or equal to a predetermined value at time t5. This triggers the controller 12 to start measuring the heart rate, the blood pressure, and the brain waves. The controller 12 measures the heart rate, the blood pressure, and the brain waves at the 10-second interval (times t6, t7, and t8), for example, after the measurement starts until the normal state is resumed. The measurement allows the storage 13 to record a pattern as a result of measuring brain waves as well as a result of measuring the heart rate and the blood pressure. The sampling time to measure the heart rate, the blood pressure, and the brain waves may be changed to be shorter than ten seconds described above. At time t9, values for the heart rate, the blood pressure, and the brain waves return to the normal state. Subsequently, the controller 12 stops measuring the brain waves and returns to the normal measurement that measures the heart rate and the blood pressure at the 10-second interval (times t10, t11, and so on).

Figure 5:
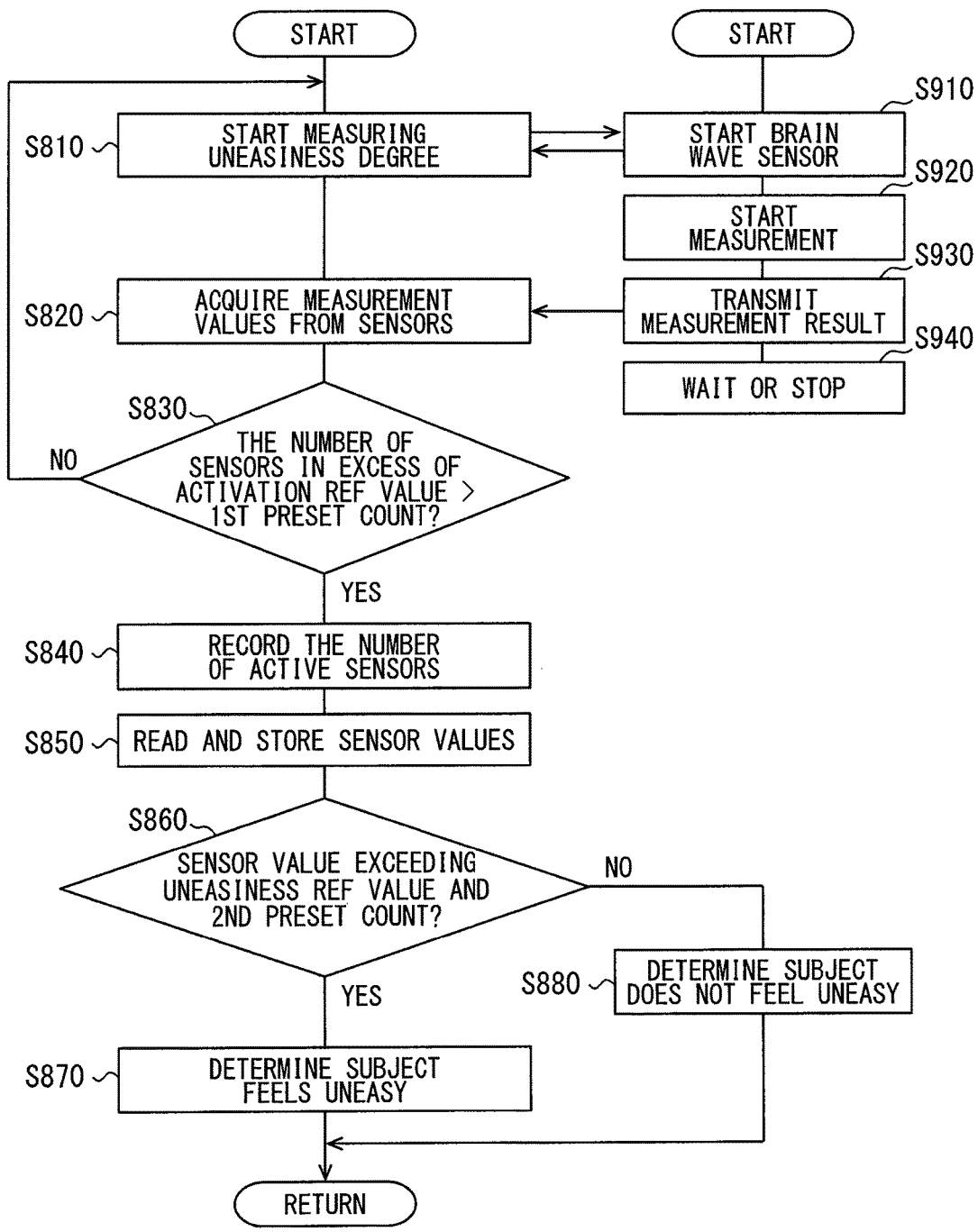
FIG. 5 is a flowchart of an uneasiness degree determination process.

With reference to a flowchart in FIG. 5, the description below explains a subroutine for a user's uneasiness degree determination process. The flowchart from S810 to S880 in FIG. 5 illustrates the control content of the user's uneasiness degree determination process in the driving control system 1. The flowchart from S910 to S940 in FIG. 5 illustrates the control content of a brain wave sensor 24 (see FIG. 10) of the brain activation region measuring instrument 23 (see FIGS. 11A and 11B). Specific configurations of the brain activation region measuring instrument 23 and the brain wave sensor 24 will be described later.

At S810 in FIG. 5, the vehicular driving control system 1 starts measuring an uneasiness degree when the vehicle starts traveling. The vehicular driving control system 1 supplies the power to the brain wave sensor 24 and outputs a measurement start directive to start the brain wave sensor 24. In response to this, the brain wave sensor 24 starts at S910. When started, the brain wave sensor 24 transmits a start response to the vehicular driving control system 1. The brain wave sensor 24 proceeds to S920 to start the measurement. The brain wave sensor 24 proceeds to S930 to transmit a measurement result to the driving control system 1 (driver situation determiner 4). The brain wave sensor 24 proceeds to S940 to wait or stop the operation.

The vehicular driving control system 1 proceeds to S820 to acquire measurement values from the brain wave sensors 24 installed at positions of the brain activation region measuring instrument 23. The vehicular driving control system 1 proceeds to S830 to determine whether the number of brain wave sensors 24 in excess of an activation reference value exceeds a first predetermined count. If the number of brain wave sensors 24 does not exceed the first predetermined count, the vehicular driving control system 1 returns to S810 to repeat the above-mentioned process and re-issues a measurement directive.

Figure 27A:
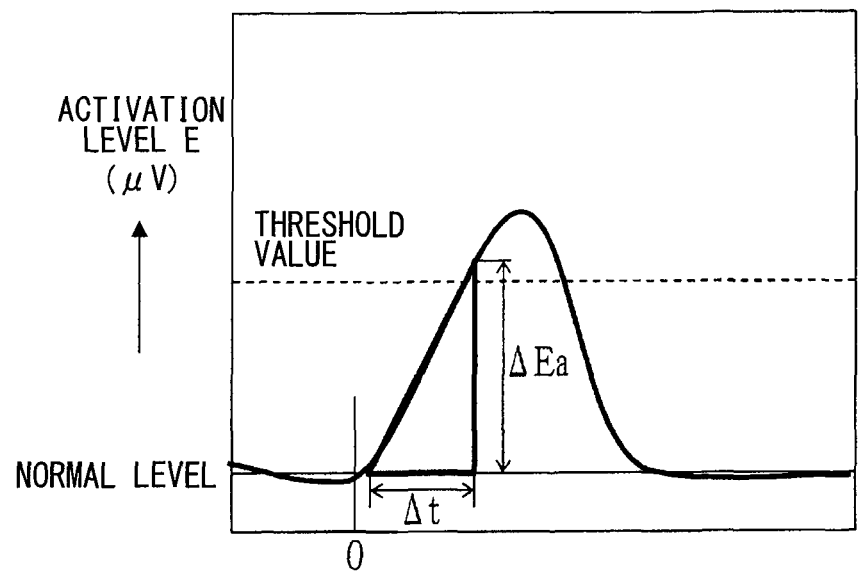
FIG. 27A is a diagram illustrating an activation reference value.
Figure 27B:
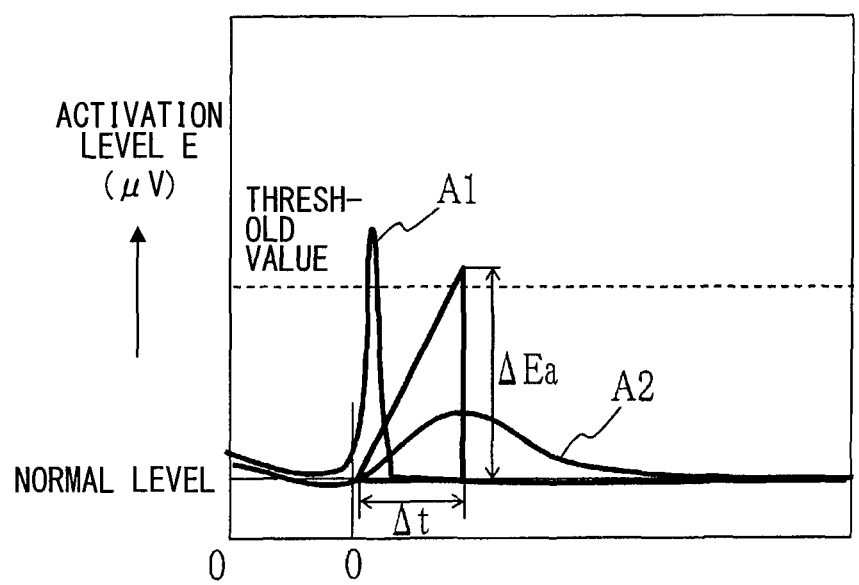
FIG. 27B is a diagram illustrating an activation reference value.

The activation reference value is provided as a criterion value to determine whether the brain activity is more activated than the normal state. As illustrated in FIG. 27A, the activation reference value is assumed to be exceeded when the voltage of a measurement signal output from the brain wave sensor 24 is higher than or equal to predetermined voltage $\Delta Ea$ and the time to continuously output the measurement signal is longer than or equal to predetermined time $\Delta t$. This can eliminate a spike-like measurement signal that rises in a short time and falls immediately by assuming the measurement signal to be a noise. As illustrated in FIG. 27B, for example, measurement signal A1 is not assumed to exceed the activation reference value because the measurement time does not continue longer than or equal to $\Delta t$. Measurement signal A2 is not assumed to exceed the activation reference value because the voltage does not change to be higher than or equal to $\Delta Ea$ within measurement time $\Delta t$. The process at S830 determines whether the vehicular driving control system 1 proceeds to the measurement of an uneasiness degree. The brain is determined to be unquestionably activated when the number of brain wave sensors 24 in excess of the activation reference value is larger than or equal to the first predetermined count.

If the number of brain wave sensors 24 exceeds the first predetermined count at S830, the vehicular driving control system 1 proceeds to "YES" and proceeds to S840 to allow the storage 13 to record the number of brain wave sensors 24 (the number of active sensors) in excess of the activation reference value. The vehicular driving control system 1 proceeds to S850 to read a measurement value from each brain wave sensor 24 and record the measurement value in the storage 13.

The controller 12 proceeds to S860 to compare measurement values of the brain wave sensors 24 with an uneasiness reference value. The vehicular driving control system 1 determines whether the number of brain wave sensors 24 in excess of the uneasiness reference value exceeds a second predetermined count. If the number of brain wave sensors 24 in excess of the uneasiness reference value exceeds the second predetermined count, the vehicular driving control system 1 proceeds to "YES" and proceeds to S870 to determine that the user (measurement subject) feels uneasy. If the number of brain wave sensors 24 in excess of the uneasiness reference value does not exceed the second predetermined count at S860, the vehicular driving control system 1 proceeds to "NO" and proceeds to S880 to determine that the user (measurement subject) does not feel uneasy.

The uneasiness reference value is provided as a criterion value used to determine that a brain activity occurs and is active enough to allow the user to sufficiently feel uneasy. The uneasiness reference value is represented as a predetermined voltage value of a measurement signal output from the brain wave sensor 24. In FIGS. 23 through 27B, the uneasiness reference value corresponds to a threshold value for an output voltage of the measurement signal output from the brain wave sensor 24. As illustrated in FIG. 27B, an output voltage of measurement signal A1 exceeds the uneasiness reference value and the continuation time of measurement signal A is shorter than predetermined time $\Delta t$. In this case, the measurement signal is processed as a noise and is not assumed to be uneasiness.

With reference to a flowchart in FIG. 6, the description below explains a subroutine to perform the driving control (automated driving or driving assistance) corresponding to road information. The driving control or the driving assistance uses emotion data about the user (driver or fellow passenger). In this case, the controller 12 uses the emotion data along with data such as a road shape to perform a process that estimates whether a road to be traveled makes the user uneasy.

Figure 6:
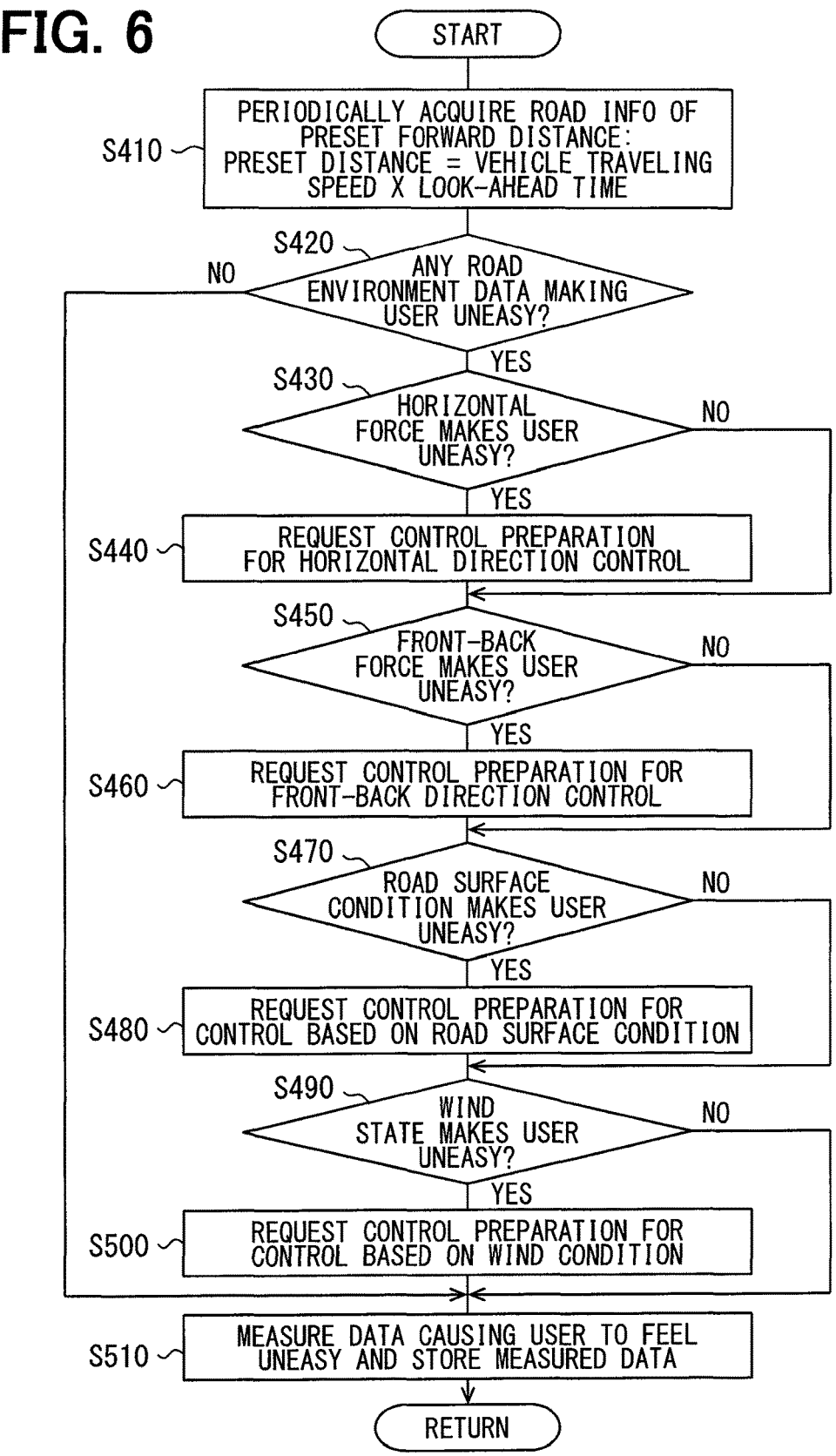
FIG. 6 is a flowchart illustrating a process to perform driving control depending on road information.

At S410 in FIG. 6, the controller 12 periodically acquires the road information about a forward predetermined distance range. The predetermined distance range is calculated and configured as a product of the vehicle traveling speed and the look-ahead time. The road information to be acquired includes information about a road shape, a speed limit, road surface information, a force of wind (crosswind), the presence or absence of a building, and a road requiring careful driving such as a school road. The controller 12 periodically acquires the information while measuring data of an uneasiness degree of the user. The user's uneasiness, if detected, is stored in the storage 13 in association with the road information. The stored data is referenced when the user data is updated later.

The controller 12 proceeds to S420 to determine whether the forward predetermined distance range includes road environment data that makes the user uneasy. If there is no road environment data that makes the user uneasy, the controller 12 proceeds to "NO" and proceeds to S510. The controller 12 performs a process to measure uneasiness data of the user and stores measurement data in the storage 13. For example, the control process according to the flowchart in FIG. 4 measures uneasiness data of the user.

If there is road environment data that makes the user uneasy at S420, the controller 12 proceeds to "YES" and proceeds to S430. At S430, the controller 12 determines whether a horizontal force makes the user uneasy. The emotion data about the user may include data indicating that the user tends to feel uneasy due to a horizontal force. In such a case, the controller 12 proceeds to "YES" and proceeds to S440 to transmit information directing or requesting a control preparation to the second driving control ECU 10 of the vehicle for horizontal direction control. This information includes the magnitude of a horizontal acceleration that makes the user uneasy. The second driving control ECU 10 controls the horizontal direction of the vehicle to limit the horizontal acceleration to a predetermined range so that the user does not feel uneasy.

The controller 12 proceeds to S450 to determine whether a front-back force makes the user uneasy. The emotion data about the user may include data indicating that the user tends to feel uneasy due to a front-back force. In such a case, the controller 12 proceeds to "YES" and proceeds to S460 to transmit information directing or requesting a control preparation to the first driving control ECU 9 of the vehicle for front-back direction control. This information includes the magnitude of a front-back acceleration that makes the user uneasy. The first driving control ECU 9 controls the front-back direction of the vehicle to limit the front-back acceleration to a predetermined range so that the user does not feel uneasy.

The controller 12 proceeds to S470 to determine whether a road surface condition makes the user uneasy. The emotion data about the user may include data indicating that the user tends to feel uneasy due to an action depending on the road surface condition such as large or frequent vertical movement. In such a case, the controller 12 proceeds to "YES" and proceeds to S480. At S480, the controller 12 transmits information directing or requesting a control preparation to the third driving control ECU 15 of the vehicle for vertical direction control. This information includes the magnitude of a vertical acceleration that makes the user uneasy. The third driving control ECU 15 controls the vertical direction of the vehicle to limit the vertical acceleration to a predetermined range so that the user does not feel uneasy.

The controller 12 proceeds to S490 to determine whether a wind state makes the user uneasy. The emotion data about the user may include data indicating that the user tends to feel uneasy due to an action of wind such as crosswind. In such a case, the controller 12 proceeds to "YES" and proceeds to S500. At S500, the controller 12 transmits information directing or requesting a control preparation to the driving control ECUs 9, 10, and 15 of the vehicle. This information includes the direction and the magnitude of an acceleration acting on the vehicle in response to an action of the wind that makes the user uneasy. The driving control ECUs 9, 10, and 15 perform vehicular driving control so that the user does not feel uneasy. The controller 12 proceeds to S510 to measure data that causes the user to feel uneasy during the actual vehicular driving control. The controller 12 stores the measured data in the storage 13.

With reference to a flowchart in FIG. 7, the description below explains a subroutine at S300 in FIG. 3. The subroutine prepares to transmit a driving condition (driving control data or control parameter) to the ECUs for driving control. The driving condition is assumed to be likely to make the driver or the fellow passenger feel uneasy. The subroutine configures a control parameter to achieve a driving control target (preference for safety or arrival time).

Figure 7:
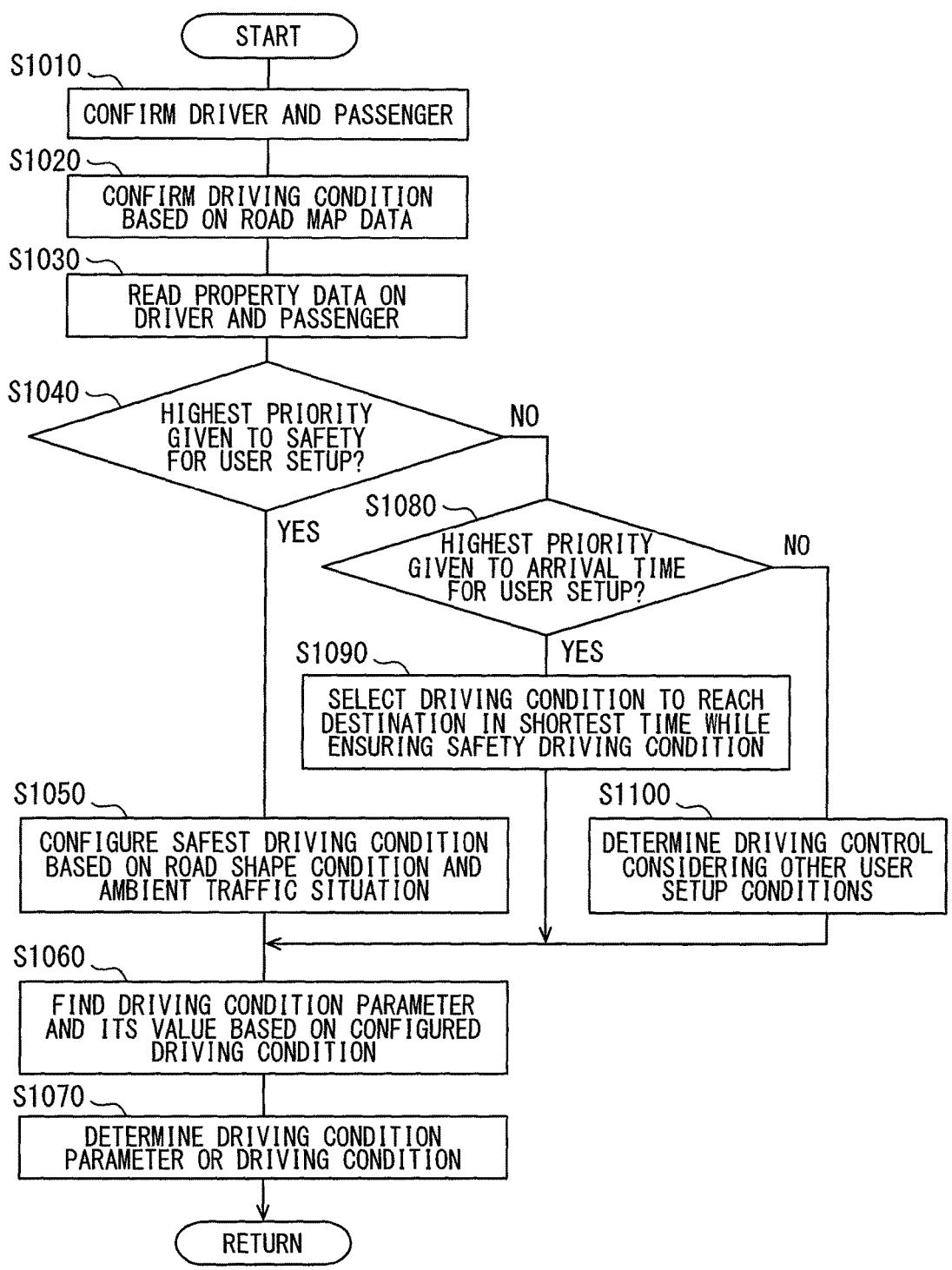
FIG. 7 is a flowchart illustrating a process that configures control parameters to achieve a driving control target (preference for safety or arrival time)

At S1010 in FIG. 7, the controller 12 confirms or recognizes the user, namely, the driver and the fellow passenger. Similarly to S30 in FIG. 2, the subroutine in FIG. 3 performs the recognition process. The controller 12 proceeds to S1020 to confirm a driving condition (road width, corner, or slope) of a road to be traveled based on road map data.

The controller 12 proceeds to S1030 to search an emotion database by using the confirmed road driving condition as a second search keyword and read property data (emotion data) about the user (driver or fellow passenger). The emotion database stores data measured and statistically processed by various sensors. The data includes data about users at normal activation levels, speeds of response to various stimuli such as vertical or horizontal acceleration, vibration, and sound, the magnitude of response (uneasiness), and the continuation time of response (uneasiness). As a result of searching the emotion database, the controller 12 acquires data (property data) capable of estimating what emotional change (uneasiness) a specific user (driver or fellow passenger) experiences on a road to be traveled.

The controller 12 proceeds to S1040 to read setup data for the user and determines whether the setup data gives the highest priority to safety. If the setup data gives the highest priority to safety, the controller 12 proceeds to "YES" and proceeds to S1050 to configure the safest driving condition from the property data for the driver and the fellow passenger based on a road shape condition and an ambient traffic situation (e.g., the number of vehicles around, a degree of congestion, or a traveling speed). At S1060, the controller 12 finds a driving condition parameter and its value based on the configured driving condition. Alternatively, the controller 12 may transmit a target driving condition to the driving control ECUs 9, 10, and 15 and allow the driving control ECUs 9, 10, and 15 to configure the driving condition parameter. At S1070, the controller 12 determines the driving condition parameter or the driving condition.

Figure 15:
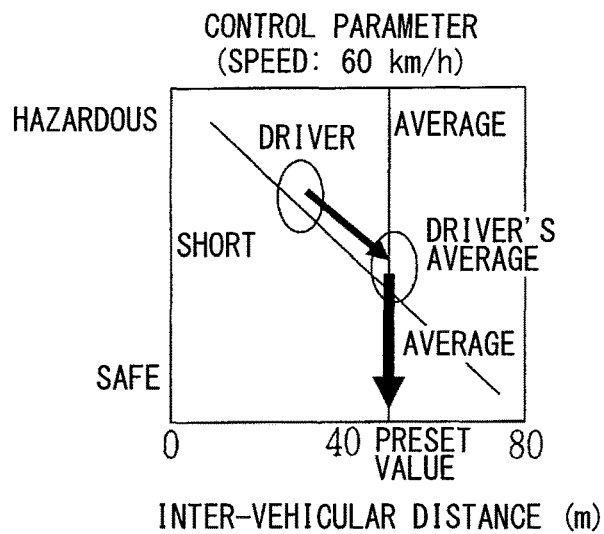
FIG. 15 is a diagram illustrating a procedure to change unsafe driving to safe driving by a driver.
Figure 16:
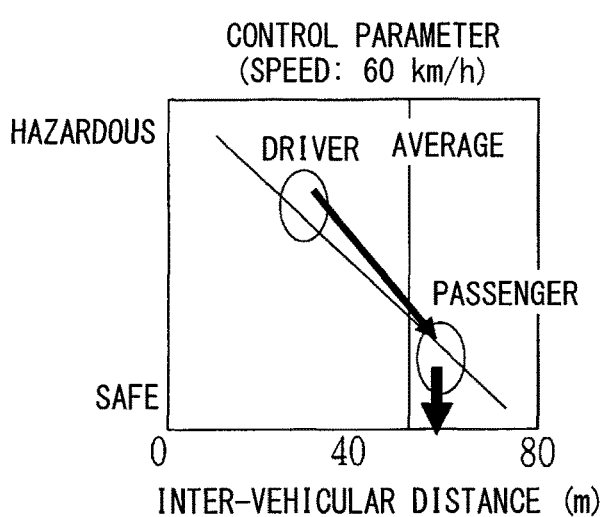
FIG. 16 is a diagram illustrating a procedure to eliminate uneasiness concerning an inter-vehicular distance from a driver and a fellow passenger.
Figure 17:
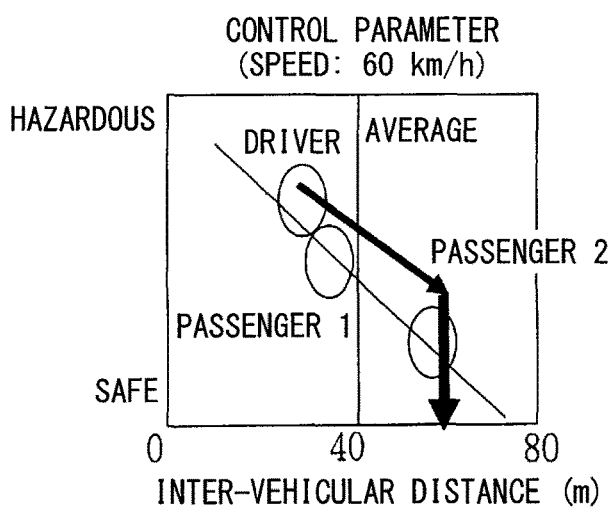
FIG. 17 is a diagram illustrating a procedure to eliminate uneasiness concerning an inter-vehicular distance from a driver and two fellow passengers.

With reference to FIGS. 15 through 17, the description below explains an example of setting the driving control so as to decrease the uneasiness. FIG. 15 illustrates a procedure to change unsafe driving of the driver to safe driving based on the inter-vehicular distance as an example. In FIGS. 15 through 17, the horizontal axis represents the inter-vehicular distance and the vertical axis represents a degree of unsafe driving (degree of hazard). The driver in FIG. 15 maintains an inter-vehicular distance shorter than an average during normal driving and indicates a high degree of hazard. The controller 12 reads data about this driver from the database to identify the degree of hazard about the driver. When the user setup is configured as "highest priority given to safety," the controller 12 increases the inter-vehicular distance to an average level such as 50 m (see S1060 in FIG. 7) to improve the safety of the driver. For this purpose, the controller 12 transmits directive data (driving condition parameter) to the inter-vehicle control ECU 8 and the first driving control ECU 9 (see S1070 in FIG. 7) so that the directive data sets the inter-vehicular distance to 50 m, for example, at a vehicle traveling speed of 60 km/h.

FIG. 16 illustrates a procedure to eliminate uneasiness concerning an inter-vehicular distance from the driver and the fellow passenger based on the inter-vehicular distance as an example. According to the example in FIG. 16, the driver does not feel uneasy even though the inter-vehicular distance is short. However, the fellow passenger feels uneasy if the inter-vehicular distance is not longer than or equal to an average. When the user setup is configured as "highest priority given to safety," the controller 12 uses an inter-vehicular distance to prevent the fellow passenger from feeling uneasy as a setup value for the inter-vehicular distance (see S1060 in FIG. 7). The controller 12 transmits directive data (driving condition parameter) to the inter-vehicle control ECU 8 and the first driving control ECU 9 (see S1070 in FIG. 7) so that the directive data sets the inter-vehicular distance to 50 m, for example, at a vehicle traveling speed of 60 km/h.

FIG. 17 illustrates a procedure to eliminate uneasiness concerning an inter-vehicular distance from the driver and two fellow passengers, namely, a total of three passengers. According to the example in FIG. 17, the driver and one of the fellow passengers do not feel uneasy even though the inter-vehicular distance is short. However, the other fellow passenger feels uneasy if the inter-vehicular distance is not longer than or equal to an average. When the user setup is configured as "highest priority given to safety," the controller 12 uses an inter-vehicular distance to prevent the other fellow passenger from feeling uneasy as a setup value for the inter-vehicular distance. When two fellow passengers are onboard, the controller 12 selects an inter-vehicular distance for the fellow passenger who prefers the longest inter-vehicular distance (see S1060 in FIG. 7). The controller 12 transmits directive data (driving condition parameter) to the inter-vehicle control ECU 8 and the first driving control ECU 9 (see S1070 in FIG. 7) so that the directive data sets the inter-vehicular distance to 60 m, for example, at a vehicle traveling speed of 60 km/h.

If the user setup does not give the highest priority to safety at S1040 in FIG. 7, the controller 12 proceeds to "NO" and proceeds to S1080 to determine whether the user setup is configured as the preference for arrival time. If the user setup is configured as the preference for arrival time, the controller 12 proceeds to "YES" and proceeds to S1090 to select a driving condition to reach a destination in a shortest time while ensuring a safety driving condition even when the arrival time is prioritized. The controller 12 can choose to travel by following a vehicle traveling at a high speed when the arrival time is prioritized.

Figure 18:
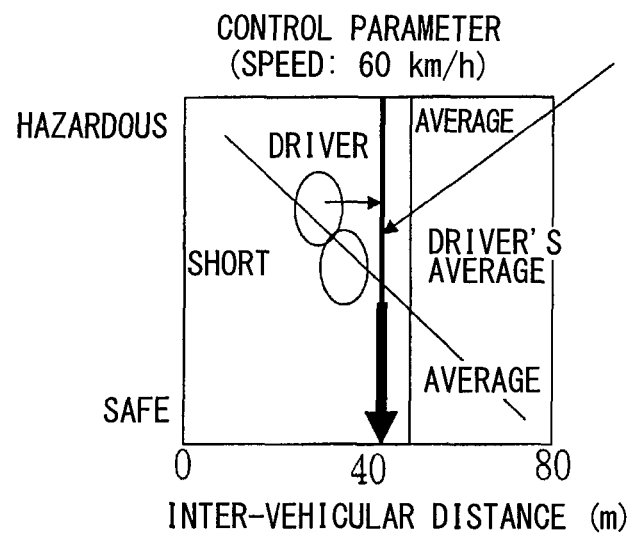
FIG. 18 is a diagram illustrating an example where a driver and a fellow passenger do not feel uneasy when an inter-vehicular distance is shorter than or equal to an average.
Figure 19:
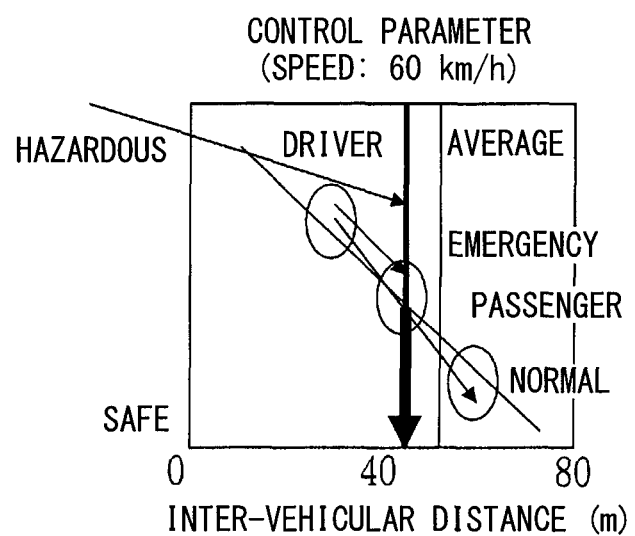
FIG. 19 is a diagram illustrating an example where a driver does not feel uneasy despite a short inter-vehicular distance but a fellow passenger feels uneasy unless an inter-vehicular distance is ensured to be longer than or equal to an average distance.

With reference to FIGS. 18 and 19, the description below explains an example of setting the driving control to decrease uneasiness when the highest priority is not given to safety. In FIGS. 18 and 19, the horizontal axis represents the inter-vehicular distance and the vertical axis represents a degree of unsafe driving (degree of hazard). According to the example in FIG. 18, the driver and the fellow passenger do not feel uneasy even when the inter-vehicular distance is shorter than or equal to an average. Also in this case, the controller 12 sets the shortest inter-vehicular distance capable of ensuring the safety of the user (see S1090 in FIG. 7). This inter-vehicular distance is shorter than the inter-vehicular distance for an average driver. The controller 12 does not shorten the inter-vehicular distance up to a limit that does not make the user uneasy.

According to the example in FIG. 19, the driver does not feel uneasy despite a short inter-vehicular distance but the fellow passenger feels uneasy unless the inter-vehicular distance is ensured to be longer than or equal to an average distance. If the driver does not feel uneasy, the controller 12 can perform the driving control when the arrival time is prioritized (especially during an emergency) by admitting to some extent that the fellow passenger may feel uneasy (see S1090 in FIG. 7). In this case, an advantageous driving control is to change an inter-vehicular distance to make the fellow passenger feel uneasy to an inter-vehicular distance to ensure safety. This driving control needs to be configured not to reflect a measurement value for the uneasiness detected from the fellow passenger. In this case, the controller 12 transmits directive data (driving condition parameter) to the inter-vehicle control ECU 8 and the first driving control ECU 9 (see S1060 and S1070 in FIG. 7) so that the directive data sets the inter-vehicular distance to 50 m, for example, at a vehicle traveling speed of 60 km/h. The inter-vehicular distance control needs to be configured not to reflect the uneasiness data about the fellow passenger.

If other user setup conditions are specified at S1080, the controller 12 proceeds to "NO" and proceeds to S1100 to determine a driving condition in consideration of the other user setup conditions.

FIGS. 13 and 14 are diagrams illustrating examples of driver property data (emotion data) about the driver and the fellow passenger. First, the driver's property data will be explained with reference to FIG. 13. The driver's property data stored includes driver's properties such as a driving tendency and an acceptable range. The driver's properties include the driver's name and characteristic values during driving. The property data concerning inter-vehicular distances stores the following characteristic values during driving. At a traveling speed of 60 km/h, for example, the forward inter-vehicular distance is 40 m (20 m shorter than an average value) and the horizontal (right-left) inter-vehicular distance is 1.0 m while the distance of 0.8 m makes the ordinary feel uneasy. At a traveling speed of 40 km/h, for example, the forward inter-vehicular distance is 10 m (10 m shorter than an average value) and the horizontal (right-left) inter-vehicular distance is 1 m while the distance of 0.8 m makes the ordinary feel uneasy. The property data as a driving style on curved roads stores the following characteristic values about the driver. The driver drives on the center of a lane at a right-hand curve and 50 cm left from the center of a lane at a left-hand curve. The other stored property data indicates in which state the driver feels uneasy in response to wobble, vibration, or sound.

FIG. 14 illustrates an example of property data about the fellow passenger. This property data is almost similar to the property data about the driver as above. The data in FIGS. 13 and 14 contains much text for the purpose of illustration. Actually, a predetermined data format is advantageously used to store the data compactly.

Figure 8:
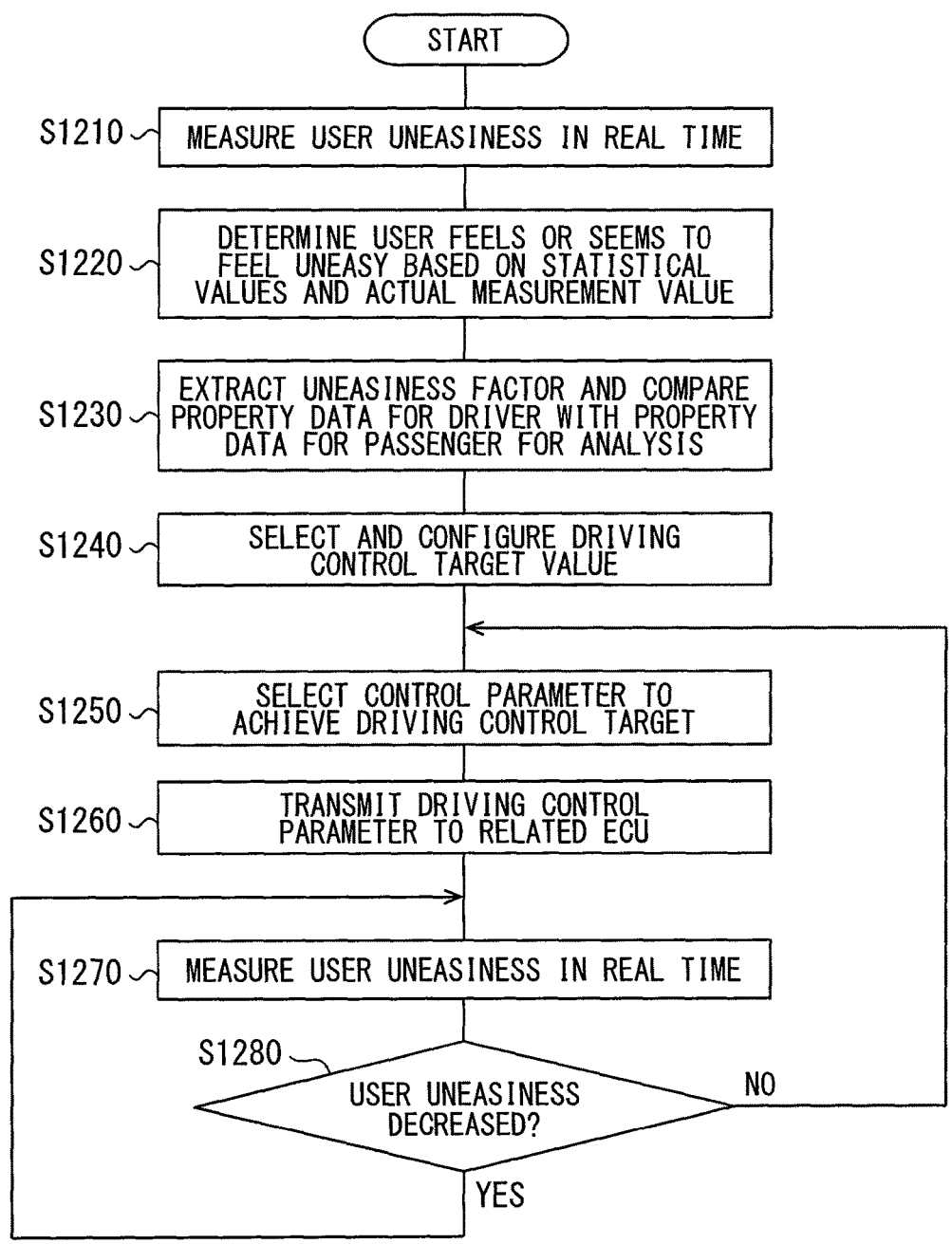
FIG. 8 is a flowchart illustrating a driving control that prevents a driver and a fellow passenger from feeling uneasy.

With reference to a flowchart in FIG. 8, the description below explains an example of the driving control that prevents the driver and the fellow passenger from feeling uneasy. At S1210, the controller 12 measures the user's uneasiness in real time. This process is performed at S60 in FIG. 2, namely, the subroutine in FIG. 5.

The controller 12 proceeds to S1220 to determine that the user feels or seems to feel uneasy (see S70 in FIG. 2) based on the statistical values and the actual measurement value measured at S1210 above. The statistical values include the uneasiness estimation data (learning value) from the road information and the uneasiness estimation data (learning value) corresponding to the user's driving style acquired at S50 in FIG. 2.

The controller 12 proceeds to S1230 to extract an uneasiness factor of the user in response to the visual sense, vertical g (g=acceleration), horizontal g, wobble (traveling position), vibration, and sound. In this case, the controller 12 compares the property data for the driver with the property data for the fellow passenger for analysis. The controller 12 proceeds to S1240 to select and configure a driving control target value (driving condition). The controller 12 proceeds to S1250 to select and configure a driving control parameter to achieve the driving control target value. This process is almost similar to the process at S1060 in FIG. 7.

The controller 12 proceeds to S1260 to transmit the driving control parameter (control range and control target) to the related ECU (inter-vehicle control ECU 8, first driving control ECU 9, second driving control ECU 10, or third driving control ECU 15). The transmitted driving control parameter is used to perform the driving control over the vehicle. The controller 12 proceeds to S1270 to measure the user's uneasiness in real time. This process can be performed at S60 in FIG. 2, namely, the subroutine in FIG. 5.

The controller 12 proceeds to S1280 to determine whether the user's uneasiness is decreased as a result of the uneasiness measurement. If the uneasiness is decreased, the controller 12 proceeds to "YES" and returns to S1270 to continue the driving control. If the uneasiness is not decreased, the controller 12 proceeds to "NO" and proceeds to S1250 to change the driving control parameter.

Figure 11A:
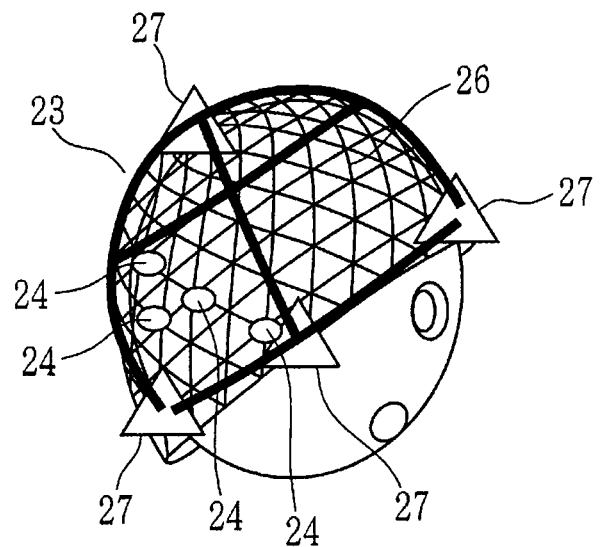
FIG. 11A is a side view illustrating a schematic configuration of a brain activation region measuring instrument.
Figure 11B:
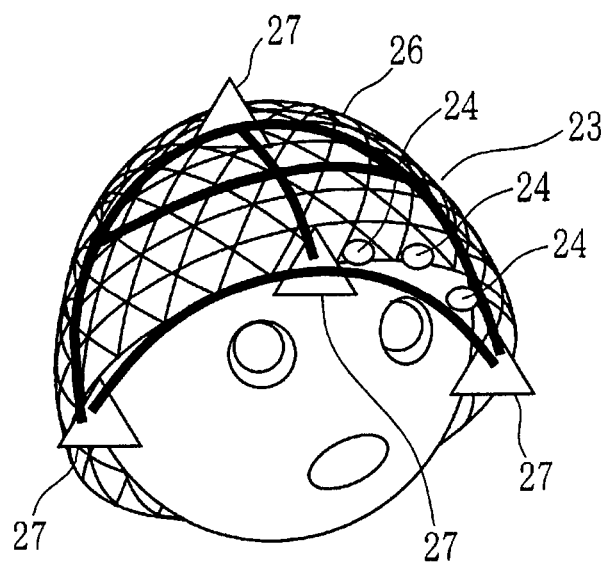
FIG. 11B is a front view illustrating a schematic configuration of the brain activation region measuring instrument.
Figure 12A:
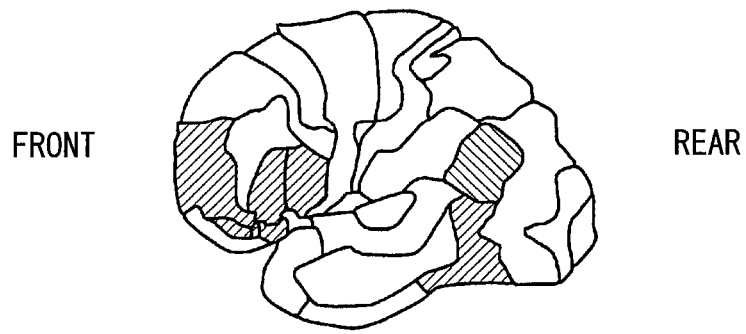
FIG. 12A is a diagram illustrating the left hemisphere of the brain.
Figure 12B:
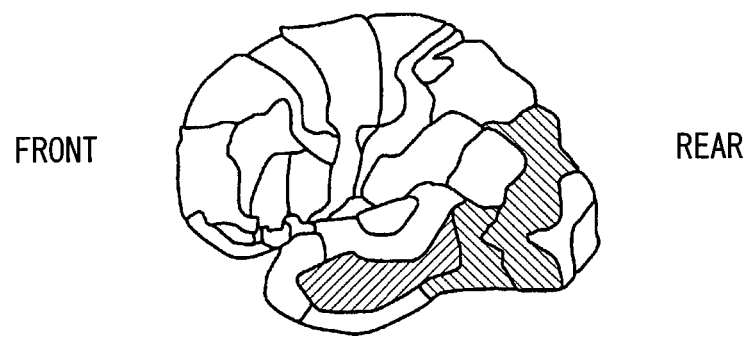
FIG. 12B is a diagram illustrating the right hemisphere of the brain.

With reference to FIGS. 11A, 11B, 12A, and 12B, the description below explains a specific configuration of the brain activation region measuring instrument 23. The brain activation region measuring instrument 23 corresponds to an example of a brain region situation measuring instrument. The brain activation region measuring instrument 23 uses a plurality of brain wave sensors 24 to measure a situation of part of the brain that is activated when uneasiness is felt. FIGS. 12A and 12B are diagrams illustrating an activated region in the brain when a person feels uneasy (scared). The activated region is hatched. FIG. 12A illustrates the left hemisphere of the brain. FIG. 12B illustrates the right hemisphere of the brain.

The embodiment aims at measuring uneasiness the user feels in the vehicle under various situations. An ordinary brain wave measurement generally provides the entire head with sensors. This method requires many sensors and increases the total cost. To solve this, the embodiment decreases the number of sensors by attaching the brain wave sensor 24 only to a point in close contact with an activation region activated when the user feels uneasy. An uneasiness degree is measured only based on whether the brain wave sensor 24 indicates a large or small measurement value.

As illustrated in FIGS. 12A and 12B, a brain region activated by uneasiness is approximately known. The brain wave sensors 24 are placed to be in close contact with the region (position) to measure situations of the region. The brain wave sensor 24 is adjustable to be repositioned on the assumption that brain activation regions vary between individuals. The brain wave sensor 24 may be removable so as to be capable of changing an attachment position to another.

FIGS. 11A and 11B illustrate schematic configurations (images) of the brain activation region measuring instrument 23. FIG. 11A is a side view of the brain activation region measuring instrument 23. FIG. 11B is an approximate front view of the brain activation region measuring instrument 23. The brain activation region measuring instrument 23 includes a hemispheric member 26 made of a mesh material, a plurality of brain wave sensors 24, and a plurality of fixing pads 27. The brain wave sensor 24 is fixed to a position inside the hemispheric member 26 so as to correspond to a brain activation region. The fixing pad 27 is provided at the end of the hemispheric member 26 and is attached to the head. Advantageously, the mesh material for the hemispheric member 26 includes an appropriately elastic material (rubber), for example. Advantageously, the fixing pad 27 is also provided at the top of the head so that the position of the brain wave sensor 24 does not easily change vertically or horizontally.

Figure 10:
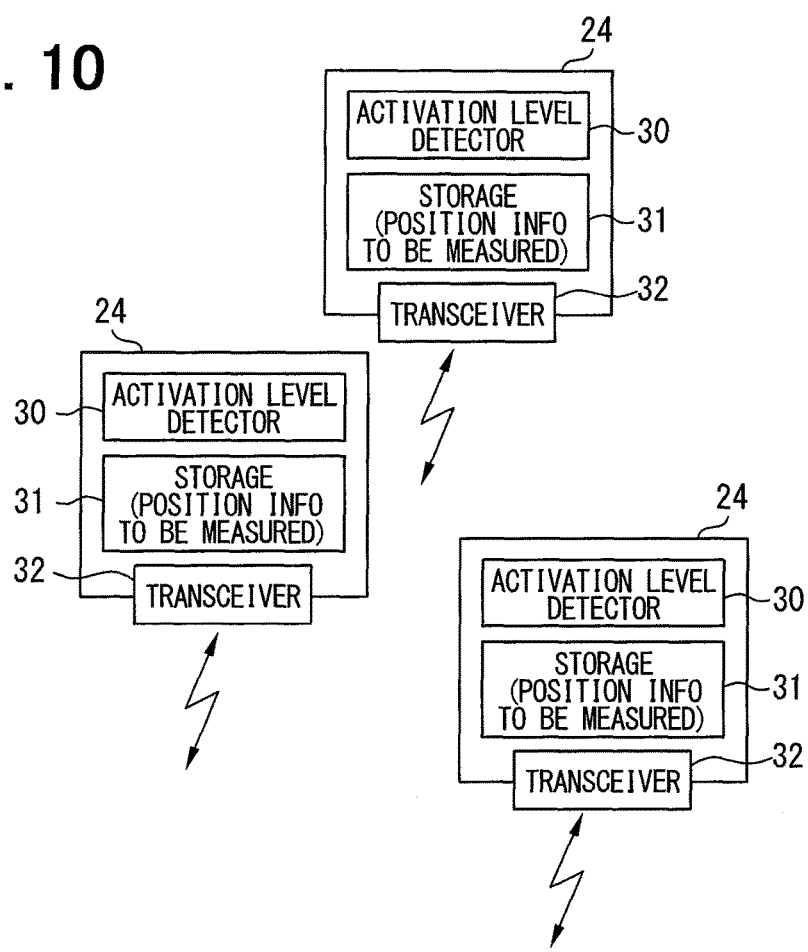
FIG. 10 is a block diagram illustrating a brain wave sensor.

FIG. 10 is a block diagram illustrating a plurality of (e.g., three) brain wave sensors 24. As illustrated in FIG. 10, each brain wave sensor 24 includes an activation level detector 30, a storage 31, and a transceiver 32. The activation level detector 30 detects an activation level of the brain activation region by measuring a variation in the blood level of oxygen in a blood vessel in response to uneasiness sensed by the brain or a minute electric current generated due to delivery and reception of ion by a brain cell. The activation level detector 30 outputs a detected activation level detection signal to the transceiver 32. The storage 31 stores position information to be measured. The transceiver 32 uses a wireless communication function to transmit the activation level detection signal from the activation level detector 30 and the position information stored in the storage 31 to the vehicular driving control system 1.

According to the embodiment, the brain wave sensor 24 (transceiver 32) uses the wireless communication function to receive a startup signal from the vehicular driving control system 1. The brain wave sensor 24 (transceiver 32) allows the activation level detector 30 to start measuring the state of a brain activation region (activation level). The transceiver 32 immediately transmits a measurement result to the vehicular driving control system 1. The brain wave sensor 24 stops operation and enters a wait state when receiving a measurement stop directive from the vehicular driving control system 1.

Figure 20:
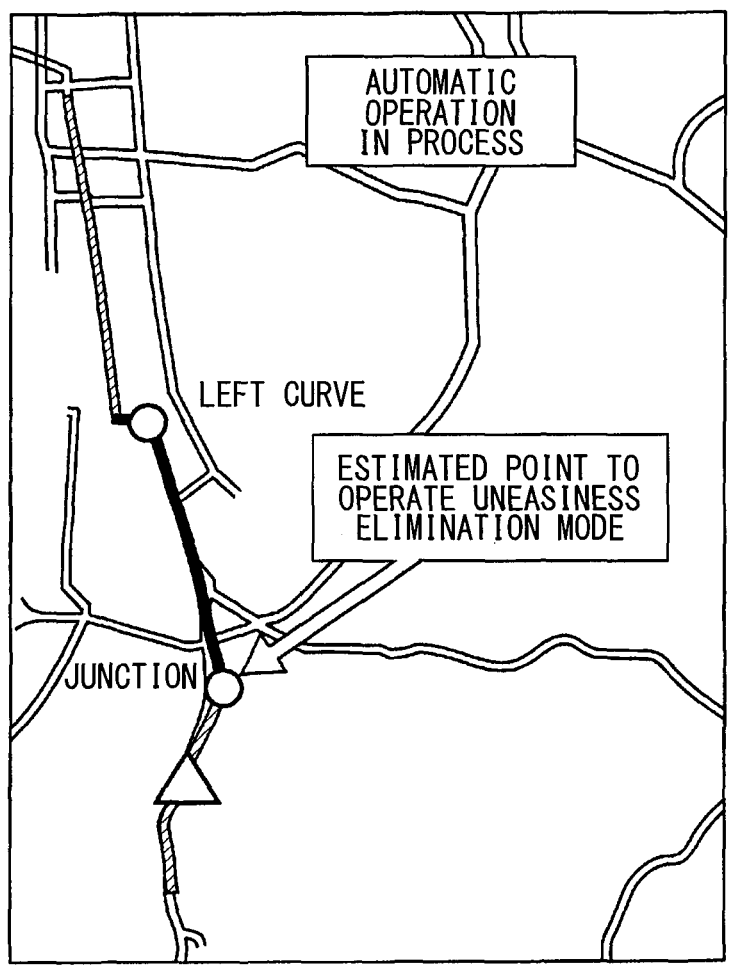
FIG. 20 is a diagram illustrating a screen view showing that a vehicle in automated driving approaches a point that causes an uneasiness elimination mode to be active.
Figure 21:
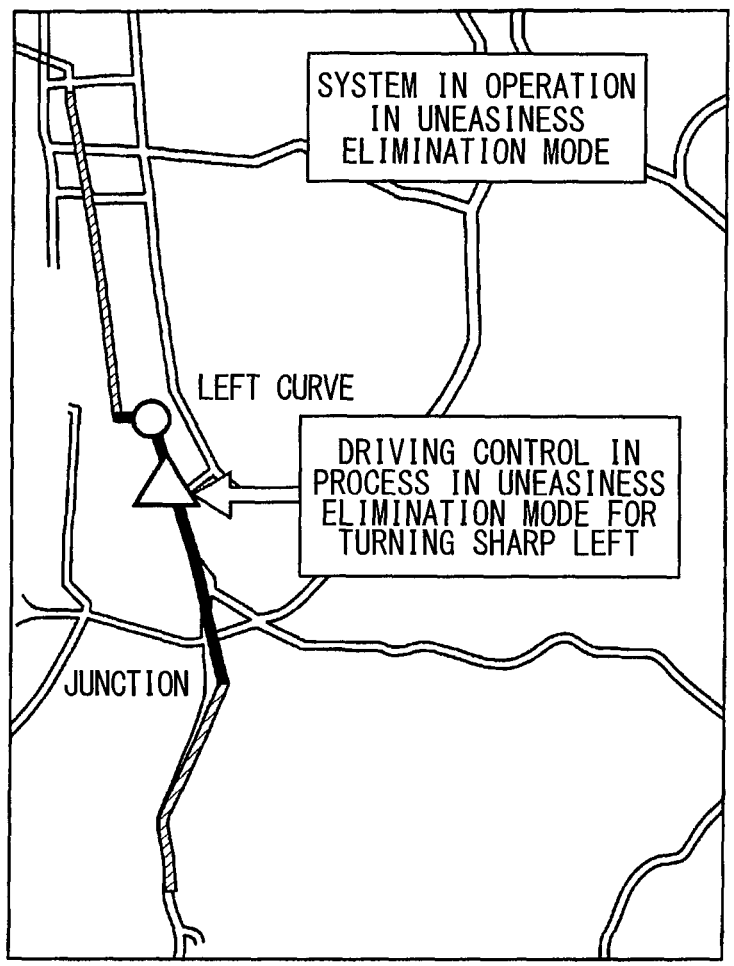
FIG. 21 is a diagram illustrating a screen view showing that the uneasiness elimination mode is active.
Figure 22:
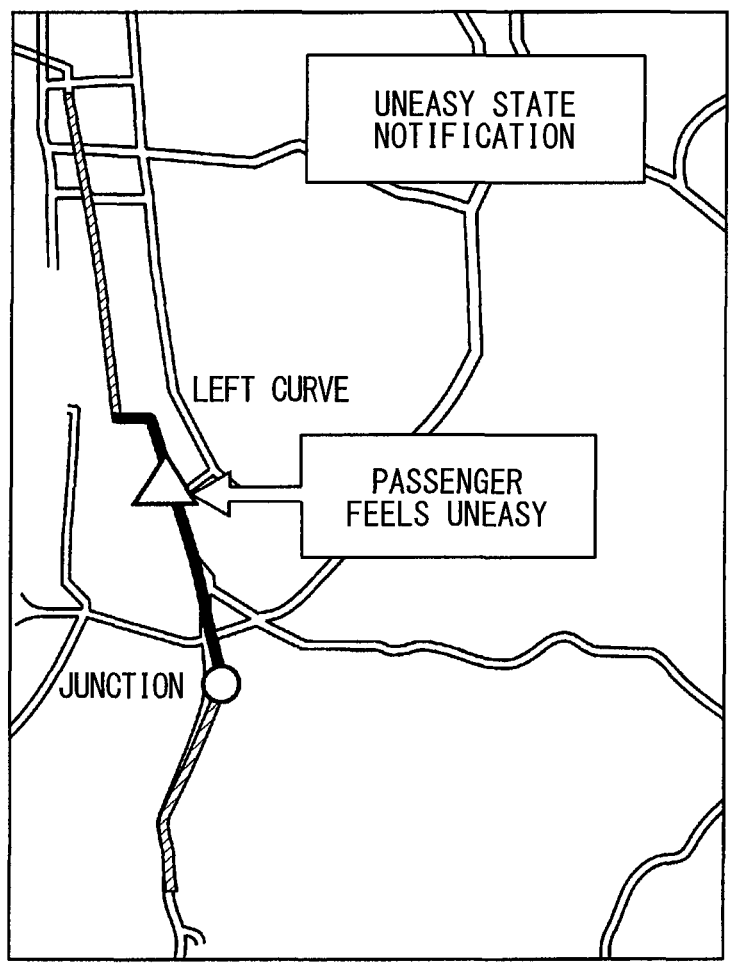
FIG. 22 is a diagram illustrating a screen view notifying a user's uneasy state during manual operation.

FIGS. 20 through 22 illustrate images during operation of the vehicular driving control system 1 according to the embodiment. FIG. 20 is a display image (an example of the display screen on the display apparatus 17) illustrating that the vehicle is in process of automated driving and approaches a point where the uneasiness elimination mode operates. In FIG. 20, a triangle represents the current position of the vehicle and messages "automated driving in process" and "estimated point to operate uneasiness elimination mode" are displayed.

FIG. 21 is a display image illustrating that the uneasiness elimination mode is in process. In FIG. 21, a triangle represents the current position of the vehicle and messages "system in operation in uneasiness elimination mode" and "driving control in process in uneasiness elimination mode for turning sharp left" are displayed. FIG. 22 is a display image illustrating notification of a user's uneasy state. In FIG. 22, a triangle represents the current position of the vehicle and messages "uneasy state notification" and "fellow passenger feels uneasy" are displayed. These images allow the user to confirm the operation of the vehicular driving control system 1. The embodiment can prevent the display concerning operations of the driving control system 1 when the user considers these displays to be unnecessary.

Figure 23:
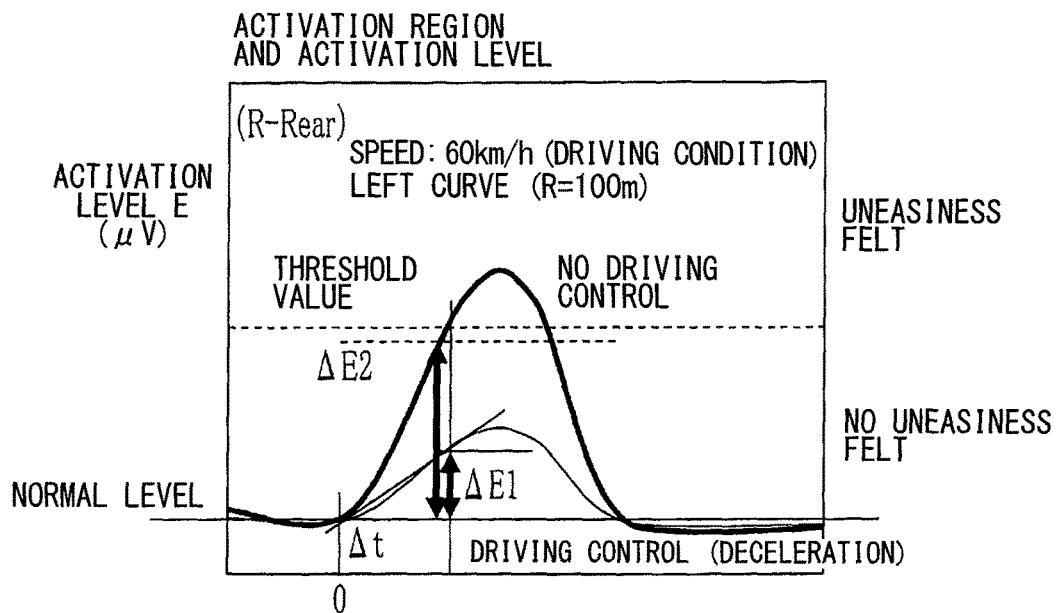
FIG. 23 is a diagram illustrating an example of measuring changes in activation level at a rear (R-Rear) of the right hemisphere of the brain.
Figure 24:
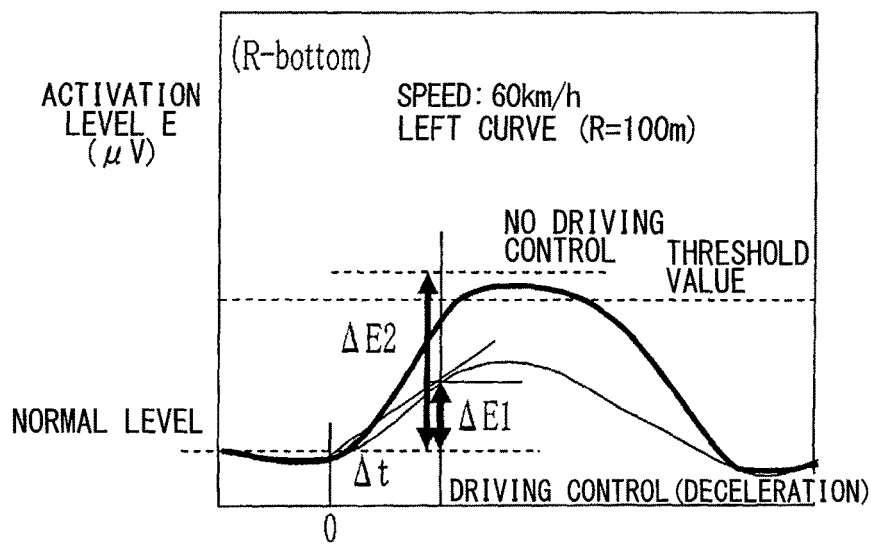
FIG. 24 is a diagram illustrating an example of measuring changes in activation level at a bottom (R-Bottom) of the right hemisphere of the brain.
Figure 25:
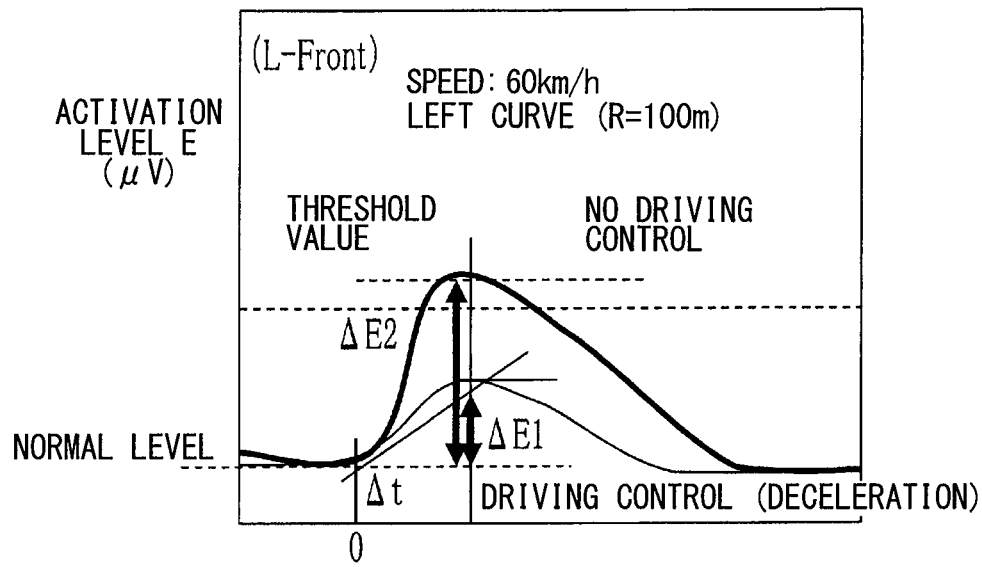
FIG. 25 is a diagram illustrating an example of measuring changes in activation level at a front (L-Front) of the left hemisphere of the brain.
Figure 26:
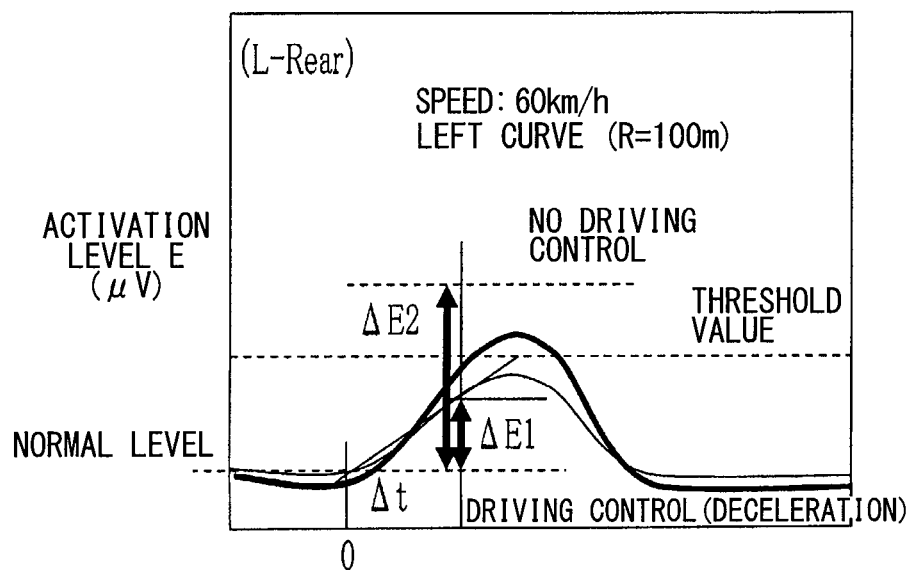
FIG. 26 is a diagram illustrating an example of measuring changes in activation level at a rear (L-Rear) of the left hemisphere of the brain.

With reference to FIGS. 23 through 26, the description below explains an example of the process at S660 in FIG. 4, namely, the process of comparing past data (stored normal-state data) about an occupant with measurement data. FIGS. 23 through 26 illustrate examples of measuring changes in brain activation levels. FIG. 23 provides an example of the measurement at a rear (R-Rear) of the right hemisphere of the brain. FIG. 24 provides an example of the measurement at a bottom (R-Bottom) of the right hemisphere of the brain. FIG. 25 provides an example of the measurement at a front (L-Front) of the left hemisphere of the brain. FIG. 26 provides an example of the measurement at a rear (L-Rear) of the left hemisphere of the brain. In each diagram, the vertical axis represents voltage E corresponding to an activation level measurement value (measurement signal output from the brain wave sensor 24). The horizontal axis represents the time. The normal level indicates a low measured voltage at the activation level because the activation level is low. Stimulation occurs at time 0 to trigger some uneasiness. The stimulation increases the voltage at the corresponding part of the brain. After a lapse of predetermined time Δt from time 0, the process measures voltage E indicating the brain activation level. This measurement can determine an activation degree of the brain activity in response to the external stimulation. The embodiment provides a brain activation reference value. As illustrated in FIG. 27A, the process determines that the activation reference value is exceeded when the voltage rises by ΔEa (V) or more during predetermined time Δt (seconds). This determination process is performed when voltage E rises and falls.

To remove a spike-like pulse noise, the process measures time Δt2 (fall time) during which voltage E indicating the brain activation level is maximized and returns to the normal level, as illustrated in FIG. 27B. The process does not determine that the activation reference value is exceeded when Δt2 is smaller than Δt. In FIG. 27B, a voltage rise in measurement signal A1 exceeds activation reference value ΔEa but fall time Δt2 is shorter than Δt. Therefore, the process does not determine that the activation reference value is exceeded.

The description below explains the normal level (see FIGS. 23 through 27B) of voltage E of a measurement signal output from the brain wave sensor 24. Advantageously, the normal level is provided as an average measurement value of brain activation level (measurement signal voltage) E measured immediately after the user gets in the vehicle. According to this definition, the normal level corresponds to data for statistically recognized states of the brain activation level when the user is onboard.

Advantageously, a normal level during rest may be also defined so as to signify an average value for measurement values of brain activation level E measured at a place other than the vehicle such as a home or a hospital capable of measuring brain waves of the user under a stable condition of the user. The user's brain activation level varies with the user's uneasiness or excitement until being onboard. The brain activation level needs to be recognized by measuring an effect of this condition. Therefore, the normal level represents data corresponding to the normal level during rest plus an onboard emotion level.

Unsuccessfully performing the appropriate safety driving control on the vehicle causes stimulation that continuously makes the driver or the fellow passenger uneasy (see a thick solid line in FIGS. 23 through 26). If the stimulation continues, the activation level of the corresponding part in the brain (voltage E indicating activation level of the brain) exceeds a threshold value (uneasiness reference value) predetermined to determine whether the user feels uneasy. The user is determined to feel uneasy unexpectedly. In FIG. 23, the voltage value corresponding to the threshold value signifies a voltage (uneasiness reference value) used to determine the uneasiness. In this case, the uneasiness induces various physical stress reactions.

The embodiment measures activation levels for parts of the brain reacting to the uneasiness under various driving conditions and learns a driving condition that induces uneasiness. A driving parameter is adjusted beforehand to provide a driving condition that causes no uneasiness when a subsequent driving condition is likely to induce the similar uneasiness. Activation levels for parts of the brain are estimated from the rise of an activation level voltage per unit time $\Delta t$ from time 0. For example, suppose that driving condition 1 causes rising voltage $\Delta E1$ per unit time and driving condition 2 causes rising voltage $\Delta E2$ per unit time. The result shows that driving condition 2 easily induces the uneasiness. Driving condition 2 can be estimated to occur based on the learning value. The user's uneasiness can be prevented by reliably performing the driving control that avoids driving under driving condition 2.

FIGS. 23 through 26 illustrate results of simulation on the four parts of the brain based on whether the driving control is performed under the driving condition of a speed of 60 km/h and a left curve (e.g., R=100 m), for example. The parts of the brain to feel uneasiness differ in rising voltage patterns. The user's uneasiness can be measured based on a measurement result from any one of the brain wave sensors 24 when activation characteristics of each part are recorded even if any of the brain wave sensors 24 to measure the brain activation region malfunction (fail).

The embodiment according to the above-mentioned configuration determines that the user feels uneasy, based on a result of measuring the user's uneasiness degree measured by the driver biological information detector 3. In this case, the embodiment determines an uneasiness factor as a source of the uneasiness based on the user's property data corresponding to a traveling situation of the vehicle. The embodiment adjusts a control degree (control parameter) of the vehicular driving control based on the determined uneasiness factor and thereby changes the vehicular driving control to decrease the user's uneasiness. The embodiment can possibly prevent the user from feeling uneasy even when the driving control is performed based on the automated driving.

According to the embodiment, the brain activation region measuring instrument 23 of the driver biological information detector 3 directly measures activation levels as situations of brain regions indicating a change in the user's emotion. The embodiment can accurately determine the user's emotion, especially, the presence or absence of the uneasiness. Further, the driver biological information detector 3 includes the sensor to measure the user's heart rate or blood pressure. A result of measuring the heart rate or blood pressure is used to determine the user's emotion (uneasiness). The embodiment can fast determine a change in the user's emotion.

The embodiment issues a notification to the driver before changing the vehicular driving control. The driver can explicitly recognize that the vehicular driving control is changed. After changing the vehicular driving control, the embodiment measures the user's uneasiness degree and finds a change in the user's uneasiness degree based on the measurement result. When the user's uneasiness is not solved, the embodiment determines the uneasiness factor as a source of the uneasiness, re-adjusts the control degree of the vehicular driving control based on the determined uneasiness factor, and then performs the vehicular driving control. The embodiment can moreover prevent the user from feeling uneasy.

The embodiment detects a traveling position in the vehicle width direction on a road based on the image information captured by the camera 5 around the vehicle and uses the radar 7 to detect an inter-vehicular distance to a preceding vehicle. The embodiment determines the presence or absence of a vehicle in a range that makes the user uneasy. The embodiment adjusts the vehicle position to decrease the user's uneasiness when determining that the user feels uneasy about the distance to the nearby vehicle. The embodiment can moreover prevent the user from feeling uneasy.

When the vehicle enters a curved road, the embodiment may determine that a centrifugal force caused by the vehicle traveling speed makes the user uneasy. In this case, the embodiment performs the driving control to decelerate when the vehicle enters the curved road. The embodiment can possibly prevent the user from feeling uneasy when the vehicle travels a curved road based on the automated driving.

The embodiment notifies the driver that the fellow passenger feels uneasy when the vehicle detects that the fellow passenger feels uneasy while the driver is performing the manual operation. The driver can correct the manual operation or improve the driver's driving technique so that the fellow passenger does not feel uneasy. The embodiment can reduce the fellow passenger's uneasiness about the driver.

The embodiment uses the fixing pad 27 of the brain activation region measuring instrument 23 as a head attachment member. Instead, the fixing pad 27 may be replaced by magic Tape®, a hairpin-shaped member, or a small comb-shaped member. A triangulation-based technique may be used as another method of measuring brain waves. In this case, the brain wave sensor 24 need not be in close contact with the brain activation region. The brain wave sensor 24 just needs to be placed at a position where information about an activation region can be easily acquired. However, this method decreases the measurement accuracy compared to the above-mentioned contact-based method. The embodiment places the brain wave sensors 24 at positions corresponding to the brain activation regions. Instead, the brain wave sensors 24 may be placed evenly all over the brain regions though the number of brain wave sensors 24 increases.

The embodiment detects brain waves as a brain region situation. Instead, a brain blood flow may be detected. The measurement of a brain blood flow permits the use of a wearable near-infrared spectrometer in contact with a human head. A sensor (e.g., a parabolic antenna) capable of measuring a minute electromagnetic wave generated from the brain may be provided above the user's head (at the vehicle ceiling) to measure magnetic fields of the head instead of brain waves. This configuration may use a shield to eliminate an electromagnetic wave noise that reaches head parts from locations other than the brain in order to accurately measure a minute electromagnetic wave generated from the brain. For example, a possible control may be provided to separate the inside of the vehicle compartment from a power supply control ECU or a high-frequency communication line or temporarily stop a wireless communications device in the vehicle compartment in synchronization with the brain wave detection timing.

FIGS. 28 through 32 illustrate a second embodiment. The mutually corresponding configurations in the first and second embodiments are designated by the same reference numerals. The first embodiment determines that the user (driver or fellow passenger) feels uneasy when a measurement value measured by the brain wave sensor 24 of the brain activation region measuring instrument 23 exceeds the predetermined threshold value (uneasiness reference value).

According to the second embodiment, the brain activation region measuring instrument 23 (brain wave sensor 24) measures the user's uneasiness degree and stores the measurement result as an onboard normal value. After the vehicle starts traveling under the condition of no force (acceleration) applied to the user, the brain activation region measuring instrument 23 (brain wave sensor 24) measures the user's uneasiness degree and stores the measurement result as a normal value while traveling. While the vehicle is traveling under the condition of a force (acceleration) applied to the user, the brain activation region measuring instrument 23 (brain wave sensor 24) measures the user's uneasiness degree and compares the measurement result with the normal value while traveling (onboard normal value). The brain activation region measuring instrument 23 determines that the user feels uneasy when a difference exceeds a predetermined value. The description below specifically explains the second embodiment.

Figure 28:
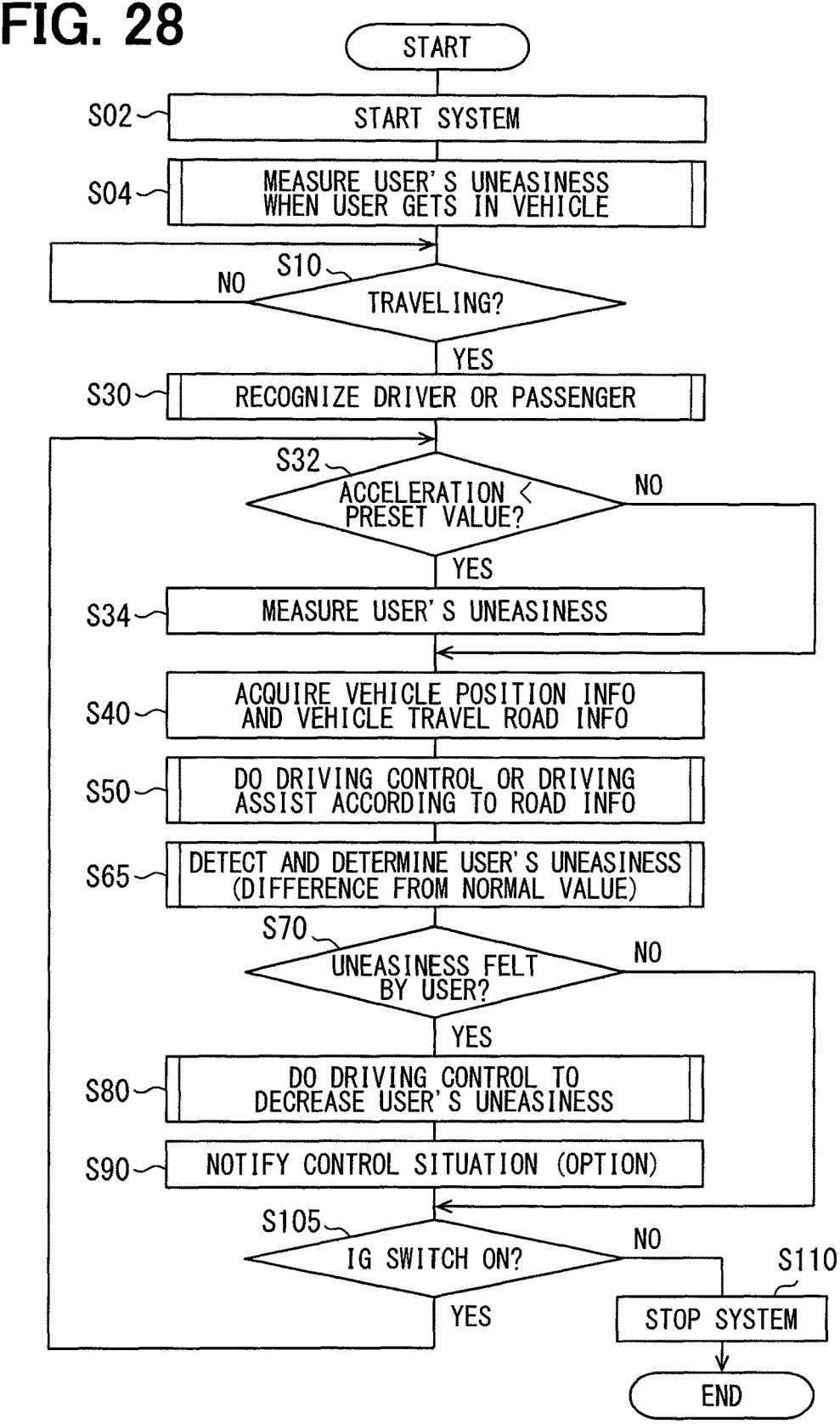
FIG. 28 is a flowchart illustrating a main control of a driving control system according to a second embodiment.
Figure 29:
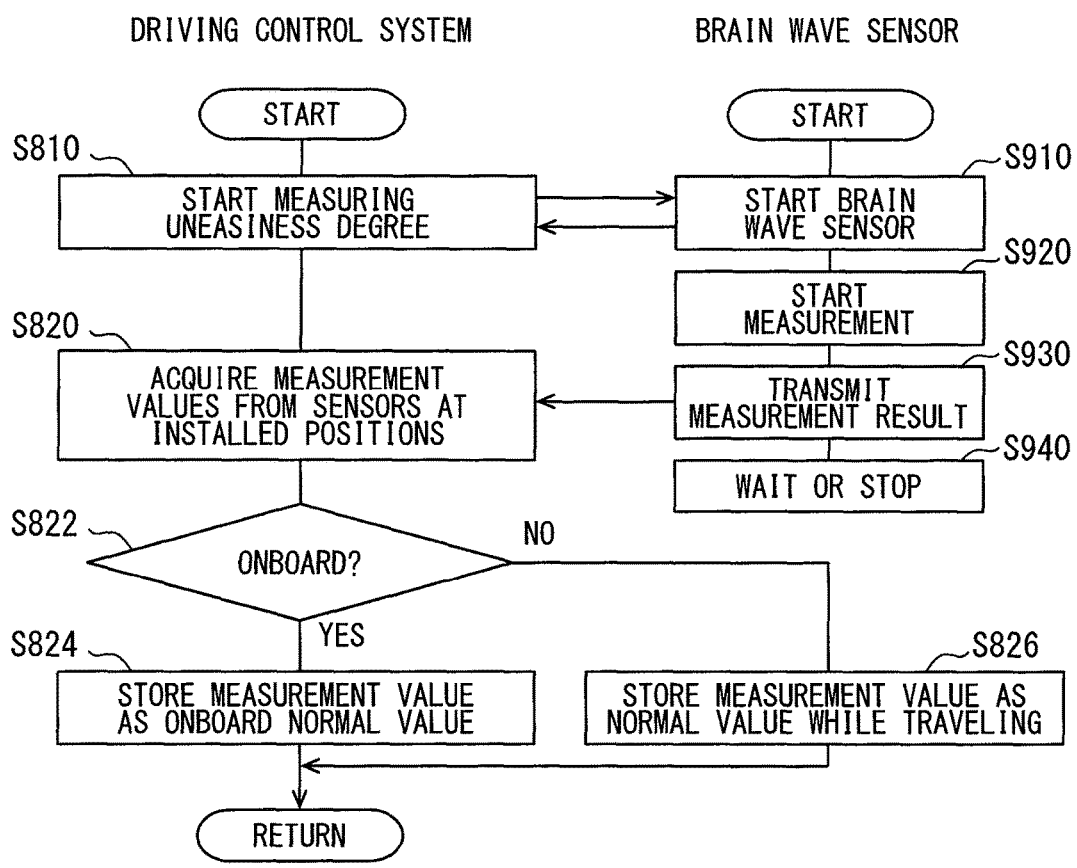
FIG. 29 is a flowchart of a control to measure user's uneasiness.

FIG. 28 replaces the flowchart in FIG. 2 according to the first embodiment. FIG. 28 is a flowchart illustrating main control of a driving control system according to the second embodiment. The control in FIG. 28 starts when an ignition switch on the vehicle is turned on, for example. At S02, the control starts the system. The control proceeds to S04. The brain activation region measuring instrument 23 (brain wave sensor 24) measures the user's uneasiness degree (its normal value) when the user gets in the vehicle. The brain activation region measuring instrument 23 stores the measurement result as an onboard normal value. Specific contents of this uneasiness measurement process will be described with reference to a subroutine flowchart in FIG. 29. The flowchart in FIG. 2 is created similarly to the flowchart in FIG. 5 according to the first embodiment. The flow from S810 to S826 in FIG. 29 represents control contents of the uneasiness measurement process for the user of the driving control system 1. The flow from S910 to S940 in FIG. 29 represents control contents of the brain wave sensor 24 of the brain activation region measuring instrument 23.

At S810 in FIG. 29, the vehicular driving control system 1 starts measuring an uneasiness degree. The vehicular driving control system 1 supplies the power to the brain wave sensor 24 of the brain activation region measuring instrument 23 and outputs a measurement start directive to start the brain wave sensor 24. In response to this, the brain wave sensor 24 starts at S910 in FIG. 29. When started, the brain wave sensor 24 transmits a start response to the driving control system 1. The control proceeds to S920. The brain wave sensor 24 starts the measurement. The control proceeds to S930. The brain wave sensor 24 transmits the measurement result to the driving control system 1 (driver situation determiner 4). The brain wave sensor 24 proceeds to S940 and enters a wait state or stops the operation.

On the driving control system 1, the control proceeds to S820 in FIG. 29 to acquire measurement values from a plurality of brain wave sensors 24 at the installation positions of the brain activation region measuring instrument 23. The control proceeds to S822 to determine whether the user gets in the vehicle, namely, the vehicle does not start traveling. If the user is onboard (S822: YES), the control proceeds to S824 and stores the measurement value as the onboard normal value in the storage 13. The process at S824 is performed when the subroutine is called at S04 in FIG. 28.

If the user is not onboard, namely, after the vehicle starts traveling at S822 (NO), the control proceeds to S826 and stores the measurement value as the normal value while traveling in the storage 13. The process at S826 is performed when the subroutine is called at S34 in FIG. 28 (to be described later).

The control proceeds to S10 in FIG. 28 and determines whether the vehicle is traveling. If the vehicle is not traveling (S10: NO), the control repeats the determination process at S10. If it is determined at S10 that the vehicle is traveling (YES), the control proceeds to S30 and performs a process to recognize the user (driver or fellow passenger). This user recognition process is performed similarly to the first embodiment (according to the subroutine in FIG. 3).

The control proceeds to S32 and determines whether an acceleration acting on the vehicle (user) is smaller than a predetermined setup value after the vehicle starts traveling. The acceleration may be smaller than the predetermined setup value, namely, no force (acceleration) may be applied to the user (S32: YES). In this case, the control proceeds to S34. At S34, the control measures the user's uneasiness degree (its normal value) when the vehicle is traveling and the brain activation region measuring instrument 23 (brain wave sensor 24) detects no force applied to the user. The control stores the measurement result as the normal value while traveling. The above-mentioned subroutine in FIG. 29 performs this uneasiness measurement process. In this case, as above, the control proceeds to NO at S822 in FIG. 29 and performs S826.

Figure 30:
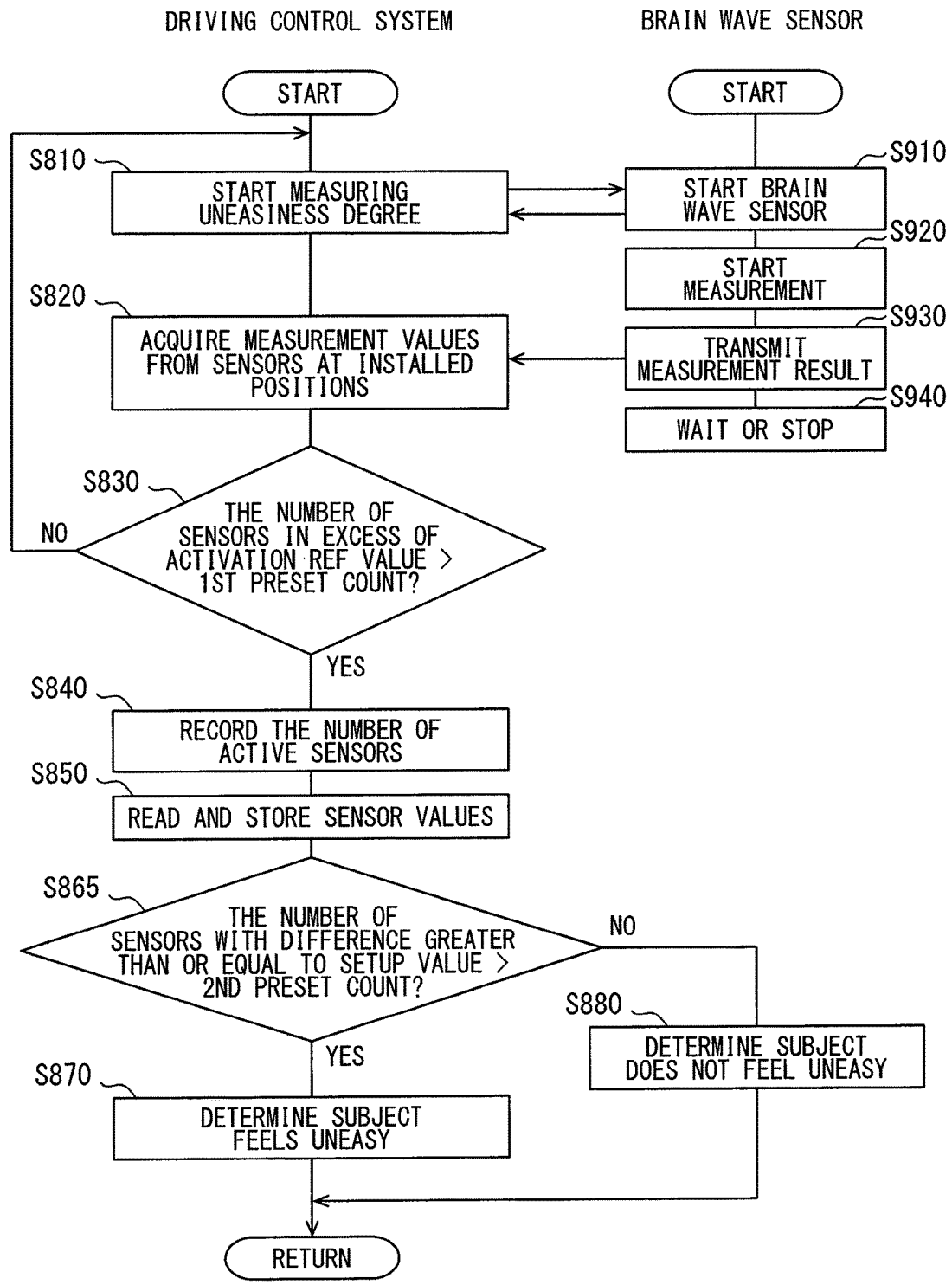
FIG. 30 is a flowchart of an uneasiness degree determination process.

Subsequently, the control performs S40 and S50 similarly to the first embodiment. The control proceeds to S65 and detects the user's uneasiness and determines the uneasiness while performing the vehicular driving control. This uneasiness detection and determination process will be described with reference to a subroutine flowchart in FIG. 30. The flowchart in FIG. 30 is created similarly to the flowchart in FIG. 5 according to the first embodiment. The flow from S810 to S880 in FIG. 30 represents control contents of the uneasiness degree determination process for the user of the driving control system 1. The flow from S910 to S940 in FIG. 30 represents control contents of the brain wave sensor 24 of the brain activation region measuring instrument 23.

The second embodiment also performs the process from S810 to S850 and the process from S910 to S940 in FIG. 30 similarly to the first embodiment.

On the driving control system 1, the control records the number of active sensors (S840) and reads measurement values from the brain wave sensors 24. The control stores the measurement values (S850) and then proceeds to S865. At S865, the control compares the measurement values from a plurality of the brain wave sensors 24 with the stored normal value while traveling and determines whether a difference is greater than or equal to a predetermined setup value. The control determines whether the number of brain wave sensors 24 exceeds the second predetermined count when the brain wave sensor 24 causes a difference greater than or equal to the setup value. For example, the control to shift the threshold value (uneasiness reference value) used for the first embodiment based on the normal value while traveling is performed when a difference between the measurement values from the brain wave sensors 24 and the normal value while traveling, when compared with each other, is determined to be greater than or equal to the setup value.

Figure 31:
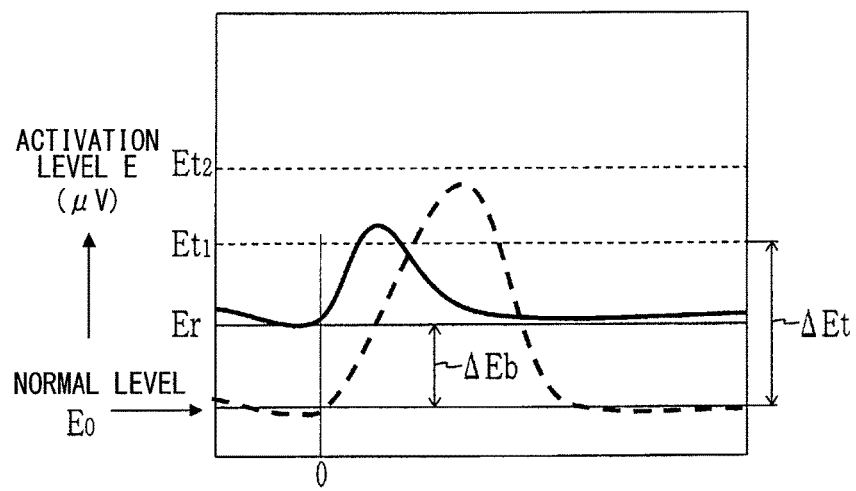
FIG. 31 is a diagram illustrating a control to shift a threshold value.

Specifically, as illustrated in FIG. 31, threshold value Et1 denotes the threshold value used for the first embodiment and threshold value Et2 denotes the shifted threshold value used for the second embodiment. Suppose that E0 denotes the normal level; ΔEt denotes an increment (for setting the threshold value) for the brain activation level; Er denotes the normal value while traveling; and bias ΔEb denotes a difference between normal value while traveling Er and normal level E0. The following relations apply:

$$Et1 = E0 + \Delta Et$$

$$Et2 = E0 + \Delta Eb + \Delta Et$$

Namely, threshold value Et2 used for the second embodiment is shifted from threshold value Et1 used for the first embodiment by bias ΔEb. At S865, the control calculates threshold value Et2 as above and then determines whether the number of brain wave sensors 24 in excess of threshold value Et2 exceeds the second predetermined count. The equation for threshold value Et2 uses the same value as the first embodiment for ΔEt (increment for the brain activation level). Instead, advantageously, ΔEt may be multiplied by variable a that varies with the value of bias ΔEb. Namely, αΔEt may replace ΔEt.

At S865, the number of brain wave sensors 24 in excess of threshold value Et2 may exceed the second predetermined count (YES). In this case, the control proceeds to S870 and determines that the user (measurement subject) feels uneasy. At S865, the number of brain wave sensors 24 causing a difference greater than or equal to the second setup value may not exceed the second predetermined count (NO). In this case, the control proceeds to S880 and determines that the user (measurement subject) does not feel uneasy.

The control then proceeds to S70 in FIG. 28 and determines whether the user feels uneasy. It may be determined that the user feels uneasy (S70: YES). In this case, the control proceeds to S80 and performs the vehicular driving control to decrease the user's uneasiness similarly to the first embodiment. The control proceeds to S90 and notifies the control situation similarly to the first embodiment when the control change necessitates the notification of the control situation.

Figure 32:
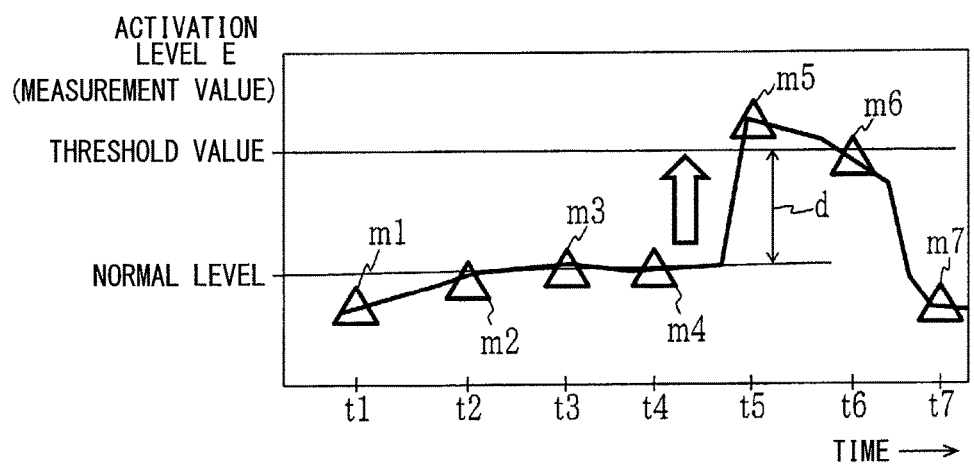
FIG. 32 is a diagram illustrating relation between a measurement value and a normal value while traveling from a brain wave sensor.

The control proceeds to S105 and determines whether the ignition switch of the vehicle is turned on. The ignition switch may be turned on (S105: YES). In this case, the control returns to S32 and repeats the above-mentioned process. While the vehicle is traveling under the condition of no force applied to the user, the process at S34 is performed at an interval of the predetermined time to cumulatively store the normal value while traveling successively (at an interval of the predetermined time). FIG. 32 is a diagram illustrating relation between a measurement value and the normal value while traveling (onboard normal value).

In FIG. 32, the user gets in the vehicle at time t1. Measurement value m1 of the brain wave sensor 24 is stored as an onboard normal value (normal value while traveling). While the vehicle is traveling under the condition of a small acceleration applied to the vehicle, measurement values m2, m3, and m4 of the brain wave sensor 24 are stored as normal values while traveling at setup times such as times t2, t3, and t4. When the vehicle starts traveling, an initial normal value while traveling almost equals the onboard normal value. At time t5, the acceleration acting on the vehicle increases. A difference between measurement value m5 of the brain wave sensor 24 and the normal value while traveling (e.g., m4) changes to be greater than or equal to the setup value (e.g., value d in FIG. 32). In this case, the user is determined to feel uneasy. The driving control is performed to eliminate the uneasiness. At time t6, measurement value m6 of the brain wave sensor 24 changes to be smaller. At time t7, measurement value m7 of the brain wave sensor 24 changes to be much smaller. A difference between measurement value m7 and the normal value while traveling (e.g., m4) changes to be smaller than the setup value.

At S105, the user may turn off the ignition switch (NO). In this case, the control proceeds to S110 and stops the driving control system 1.

At S70, the user may not feel uneasy (NO). In this case, the control proceeds to S105 and repeats the above-mentioned control.

The other configuration of the second embodiment equals the configuration of the first embodiment. Therefore, the second embodiment can also provide the same function effect as the first embodiment. Particularly, the second embodiment can provide the function effect as follows. When the user gets in the vehicle, for example, the user's mental status may be already uneasy due to other factors (e.g., an uneasy or sad event before entry into the vehicle). In such a case, the brain activation level related to the uneasiness increases. The brain activation region measuring instrument 23 (brain wave sensor 24) measures the user's uneasiness degree to find that the measurement value (voltage) of the brain wave sensor 24 is much higher than the normal value (see the solid line in FIG. 31). Therefore, the first embodiment may frequently perform the vehicle driving control to decrease the user's uneasiness because just applying a small force (acceleration) to the user (vehicle) allows the measurement value of the brain wave sensor 24 to exceed threshold value Et1 (uneasiness reference value) while the vehicle is traveling. This may annoy the user because the vehicle driving control is performed though the user does not feel uneasy so much.

According to the second embodiment, however, the brain wave sensor 24 measures the user's uneasiness degree when the user gets in the vehicle. The brain wave sensor 24 stores the measurement result as an onboard normal value. The brain wave sensor 24 measures the user's uneasiness degree after the vehicle starts traveling under the condition of no force applied to the user. The brain wave sensor 24 stores the measurement result as a normal value while traveling. While the vehicle is traveling to apply a force (acceleration) to the user, the brain wave sensor 24 measures the user's uneasiness degree for the brain activation region measuring instrument 23 to measure the user's uneasiness degree. The brain wave sensor 24 compares the measurement result with the normal value while traveling. The user is determined to feel uneasy when a difference is greater than or equal to the setup value, namely, the measurement value of the brain wave sensor 24 exceeds shifted threshold value Et2. This configuration determines that the user is not uneasy because the measurement value of the brain wave sensor 24 does not exceed threshold value Et2 even though the user's mental status is already uneasy due to other factors and the measurement value is much higher than the normal value (see the solid line in FIG. 31) when the user gets in the vehicle. This can prevent the uneasiness determination from occurring frequently and prevent the driving control from being performed frequently.

The brain activation level related to the uneasiness increases when the user feels uneasy due to an uneasy or sad event before the user gets in the vehicle. In this case, threshold value Et2 is shifted by bias ΔEb in the direction for addition as above. The brain activation level related to the uneasiness decreases when the user feels especially happy. In this case, threshold value Et2 is advantageously shifted by the bias in the direction for subtraction.

The second embodiment detects the onboard normal value and the normal value while traveling and shifts the threshold value (uneasiness reference value) for the uneasiness determination based on the normal value while traveling. The present disclosure however is not limited thereto. It may be possible to calculate a difference (voltage difference) between the measurement value and the normal value while traveling output from the brain wave sensor 24 and determine the uneasiness based on whether the calculated difference is greater than a setup value (uneasiness criterion value).

It may be also possible to selectively perform the control to fix the threshold value (uneasiness reference value) for uneasiness determination in the first embodiment and the control to shift the threshold value (uneasiness reference value) for uneasiness determination based on the normal value while traveling in the second embodiment depending on user situations. Advantageously, for example, the control to fix the threshold value in the first embodiment is performed when bias value ΔEb (see FIG. 31) is small (smaller than or equal to the setup value). This control is changed to the control to shift the threshold value in the second embodiment when bias value ΔEb exceeds the setup value.

While there have been described specific embodiments and configurations of the present disclosure, the disclosure is not limited to the above-mentioned embodiments and configurations. The scope of embodiments and configurations related to the disclosure also includes an embodiment and a configuration resulting from appropriately combining technical portions disclosed in different embodiments and configurations.

What is claimed is:

1. A vehicular driving control system for performing vehicular driving control with automated driving and/or driving assistance, the vehicular driving control system comprising:
   a driver operation measuring instrument that measures driving operation of a driver;
   a user uneasiness degree measuring instrument that measures how large a degree of uneasiness of a user is; and
   a driving control apparatus that,
      on condition of the user determined to feel uneasy based on a result of measuring the user uneasiness degree measured by the user uneasiness degree measuring instrument, determines an uneasiness factor serving as a source of the uneasiness based on user property data in relation to a traveling situation of a vehicle, and
      based on the determined uneasiness factor, adjusts a control degree of the vehicular driving control, and changes the vehicular driving control so as to decrease the uneasiness of the user,
   wherein:
   the driving control apparatus is configured to issue a notification to the driver before changing the vehicular driving control; and
   the driving control apparatus is further configured to:
      after changing the vehicular driving control, cause the user uneasiness degree measuring instrument to perform measurement of the uneasiness degree of the user to find a change in the uneasiness degree of the user based on a result of the measurement,
      if the uneasiness of the user remains unsolved, determine the uneasiness factor serving as the source of the uneasiness and readjust the control degree of the vehicular driving control based on the determined uneasiness factor.

2. The vehicular driving control system according to claim 1, wherein
   the user uneasiness degree measuring instrument includes a brain region situation measuring instrument that directly measures a situation of a plurality of brain regions indicating a change in emotion of the user.

3. The vehicular driving control system according to claim 1, further comprising:
   a widthwise traveling position detection apparatus that detects a traveling position on a road in a vehicle width direction; and
   an inter-vehicular distance detection apparatus that detects an inter-vehicular distance to a preceding vehicle,
   wherein
   the driving control apparatus determines presence or absence of a vehicle in a range making the user feel uneasy and adjusts a vehicle position to decrease the uneasiness of the user when the user is determined to feel uneasy about a distance to a nearby vehicle.

4. The vehicular driving control system according to claim 1, wherein:
   when the driving control apparatus determines that a centrifugal force caused by a vehicle traveling speed in vehicle entry into a curved road makes the user uneasy, the driving control apparatus provides the driving control so that the vehicle decelerates to enter the curved road.

5. The vehicular driving control system according to claim 1, wherein
   when the vehicle detects that a fellow passenger feels uneasy while manual driving is being performed by the driver, the driving control apparatus notifies the driver that the fellow passenger feels uneasy.

6. The vehicular driving control system according to claim 2, wherein:
   the brain region situation measuring instrument includes a brain wave sensor placed so as to correspond to an activation region in a head, the activation region being a region to be activated in response to uneasiness; and
   the driving control apparatus determines the uneasiness of the user based on a measurement value measured by the brain wave sensor.

7. The vehicular driving control system according to claim 6, wherein:
   a measurement value measured by the brain wave sensor while no force is applied to the user during traveling after the vehicle starts traveling is stored as a normal value by the driving control apparatus;

the driving control apparatus makes comparison between a measurement value measured by the brain wave sensor while a force is applied to a user during vehicle traveling and the normal value; and the driving control apparatus determines that the user feels uneasy when a difference between both the values is greater than or equal to a setup value.

* * * * *